United States Patent
Anderson et al.

(10) Patent No.: US 10,695,761 B2
(45) Date of Patent: Jun. 30, 2020

(54) MICROFLUIDIC DEVICE WITH MULTIPLE TEMPERATURE ZONES AND ENHANCED TEMPERATURE CONTROL

(71) Applicant: Sharp Life Science (EU) Limited, Oxford (GB)

(72) Inventors: Sally Anderson, Oxford (GB); Pamela Ann Dothie, Oxford (GB); Philip Mark Shryane Roberts, Oxford (GB)

(73) Assignee: Sharp Life Science (EU) Limited, Oxford (GB)

( * ) Notice: Subject to any disclaimer, the term of this patent is extended or adjusted under 35 U.S.C. 154(b) by 518 days.

(21) Appl. No.: 15/607,940

(22) Filed: May 30, 2017

(65) Prior Publication Data

US 2018/0345279 A1 Dec. 6, 2018

(51) Int. Cl.
*B01L 3/00* (2006.01)
*B01L 7/00* (2006.01)
(Continued)

(52) U.S. Cl.
CPC ..... *B01L 3/50273* (2013.01); *B01L 3/502792* (2013.01); *B01L 7/525* (2013.01);
(Continued)

(58) Field of Classification Search
CPC ......... B01L 2400/0427; B01L 3/50273; B01L 7/525; B01L 2300/18; B01L 3/502792;
(Continued)

(56) References Cited

U.S. PATENT DOCUMENTS 6,565,727 B1 5/2003 Shenderov
6,911,132 B2 6/2005 Pamula et al.
(Continued)

FOREIGN PATENT DOCUMENTS

| JP | 2006329901 A | 12/2006 |
|---|---|---|
| JP | 2010503516 A | 2/2010 |
| JP | 2012230105 A | 11/2012 |
| WO | WO 2008051310 A2 | 5/2008 |
| WO | WO 2008120135 | 10/2008 |

OTHER PUBLICATIONS

"Digital microfluidics: is a true lab-on-a-chip possible?", R.B. Fair, Microfluid Nanofluid (2007) 3:245-281).
Extended European Search Report of EP Application No. 18174362.6 dated Oct. 22, 2018.

*Primary Examiner* — Lyle Alexander
*Assistant Examiner* — Bryan Kilpatrick
(74) *Attorney, Agent, or Firm* — Renner, Otto, Boisselle & Sklar, LLP

(57) ABSTRACT

A microfluidic system is configured for enhanced temperature control by combining spatial and temporal temperature control. The microfluidic system includes an electro-wetting on dielectric (EWOD) device comprising an element array configured to receive one or more liquid droplets, the element array comprising a plurality of individual array elements; a control system configured to control actuation voltages applied to the element array to perform manipulation operations of the liquid droplets; and a plurality of thermal control elements located at different spatial locations along the EWOD device, at least one of the thermal control elements being variable in temperature with respect to time. The control system includes a thermal control unit configured to control temperatures of the thermal control elements to generate a plurality of thermal zones located at different spatial locations along the EWOD device, at least one of the thermal zones being variable in temperature with respect to time.

19 Claims, 25 Drawing Sheets

(51) Int. Cl.
*C12Q 1/686* (2018.01)
*G02B 26/00* (2006.01)

(52) U.S. Cl.
CPC ............ *C12Q 1/686* (2013.01); *G02B 26/005* (2013.01); *B01L 2200/147* (2013.01); *B01L 2300/18* (2013.01); *B01L 2400/0427* (2013.01)

(58) Field of Classification Search
CPC ................. B01L 7/54; B01L 2200/147; B01L 2300/0645; B01L 2300/0816; B01L 3/502784; G01N 27/44791; G02B 26/005
See application file for complete search history.

(56) References Cited

U.S. PATENT DOCUMENTS

| | | |
|---|---|---|
| 7,163,612 B2 | 1/2007 | Sterling et al. |
| 7,531,072 B2 | 5/2009 | Roux et al. |
| 9,452,433 B2 | 9/2016 | Shenderov et al. |
| 9,517,469 B2 | 12/2016 | Shenderov et al. |
| 2010/0140093 A1 | 6/2010 | Pamula et al. |
| 2011/0268151 A1* | 11/2011 | Hadwen ............ B01L 3/502792 374/141 |
| 2012/0264932 A1* | 10/2012 | Van Dam ............. B01J 19/0093 536/122 |
| 2015/0253284 A1 | 9/2015 | Sudarsan et al. |
| 2017/0080428 A1 | 3/2017 | Shenderov et al. |

\* cited by examiner

Fig. 1: PRIOR ART

Fig. 5
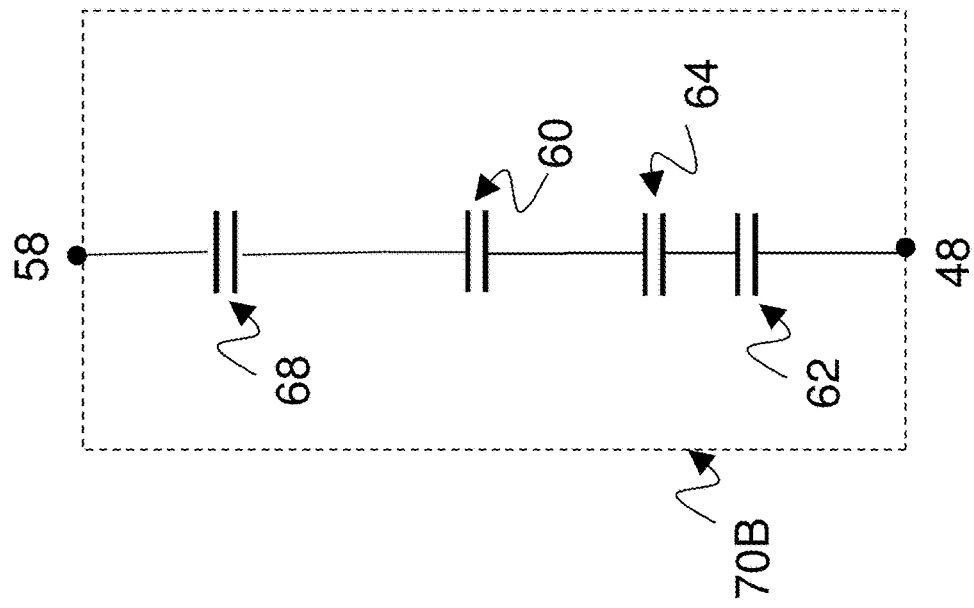
Figure 5B
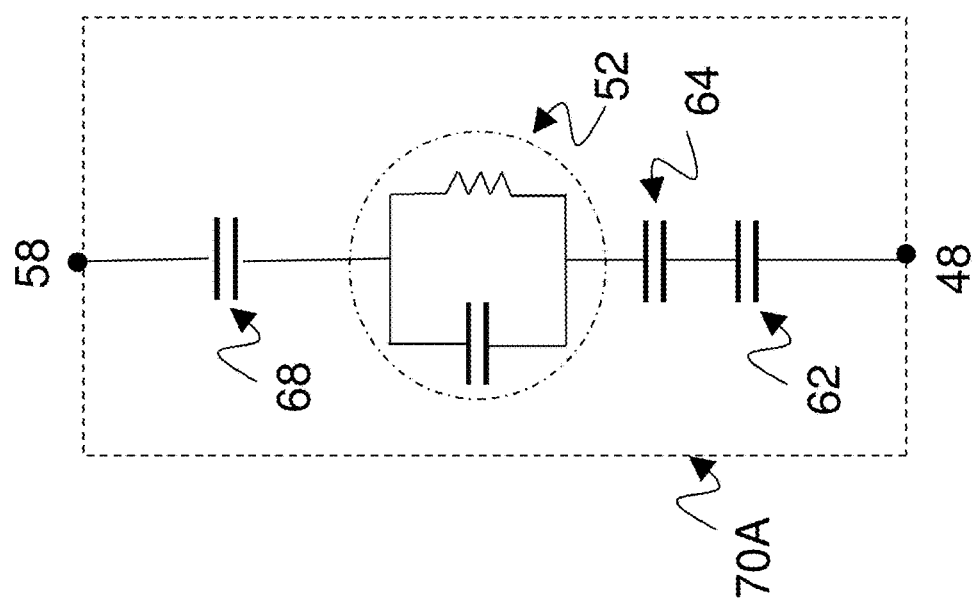
Figure 5A

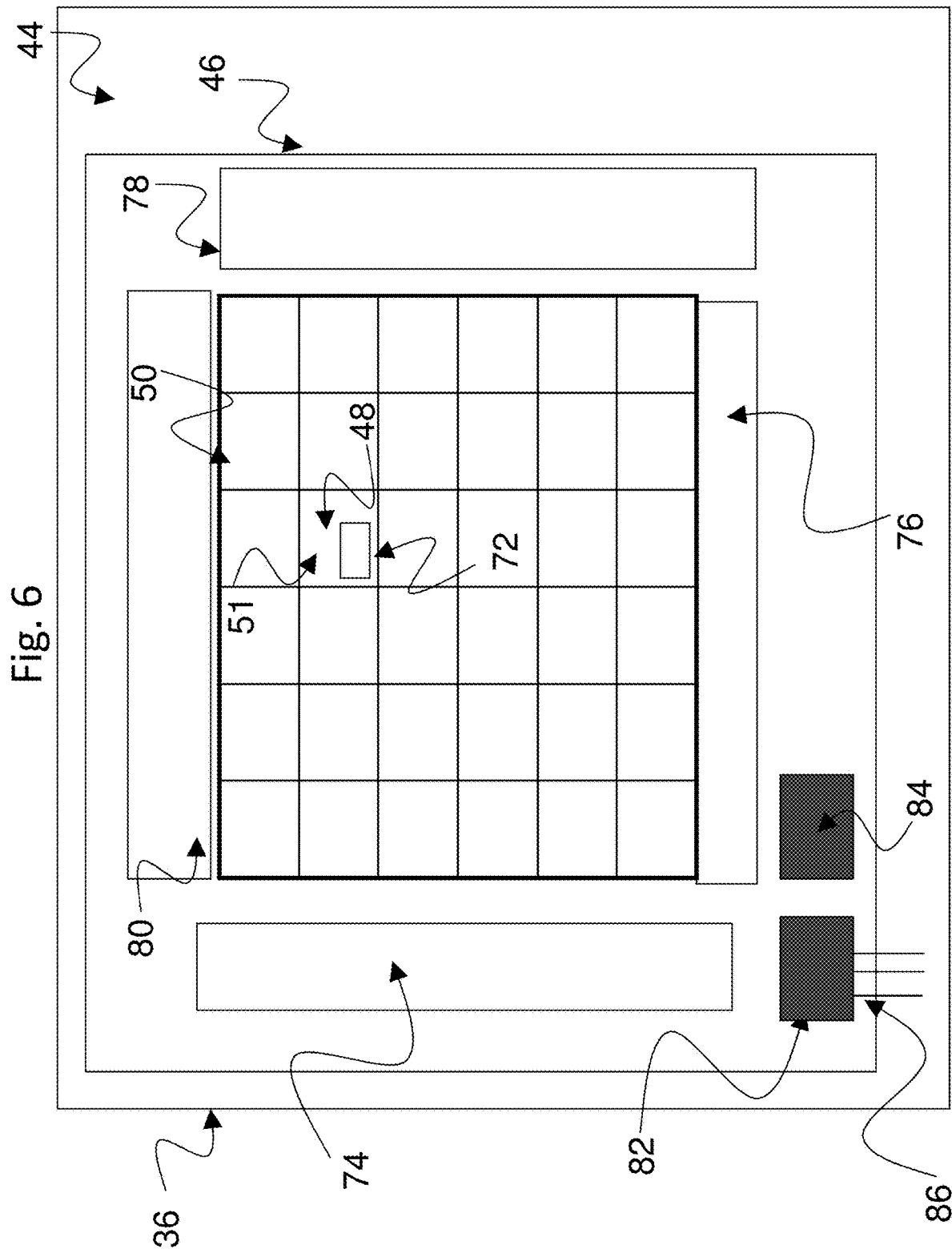

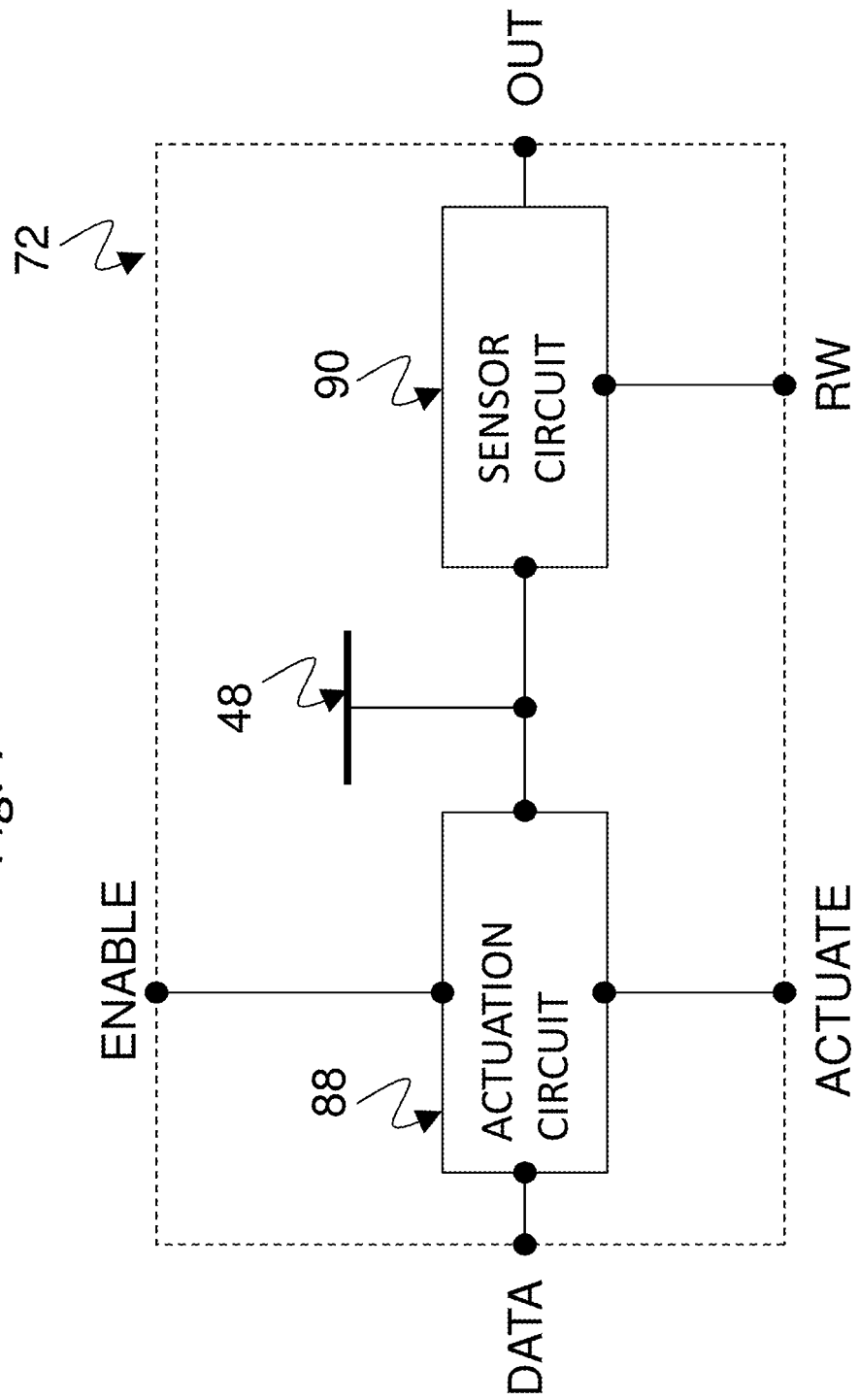

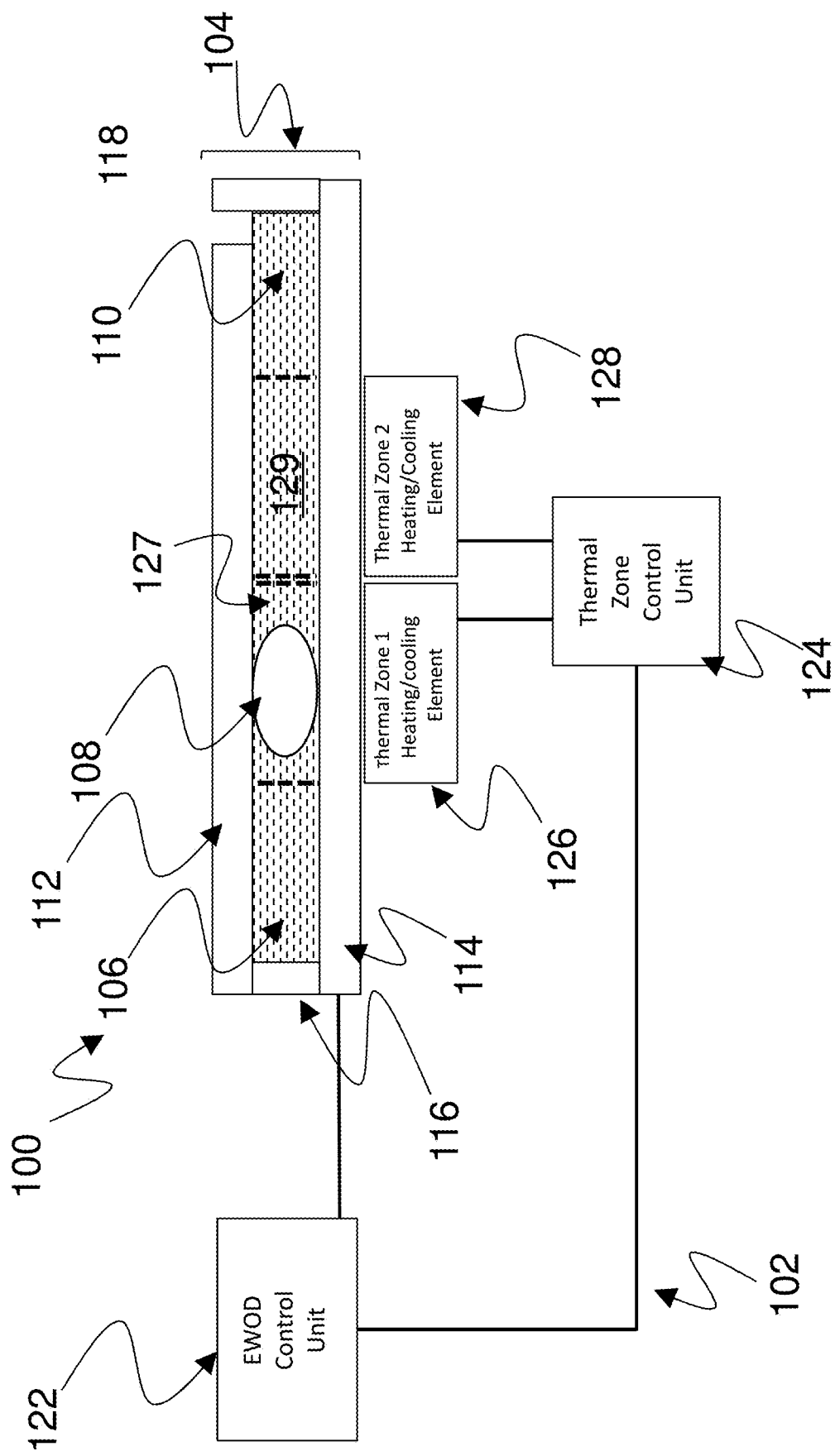

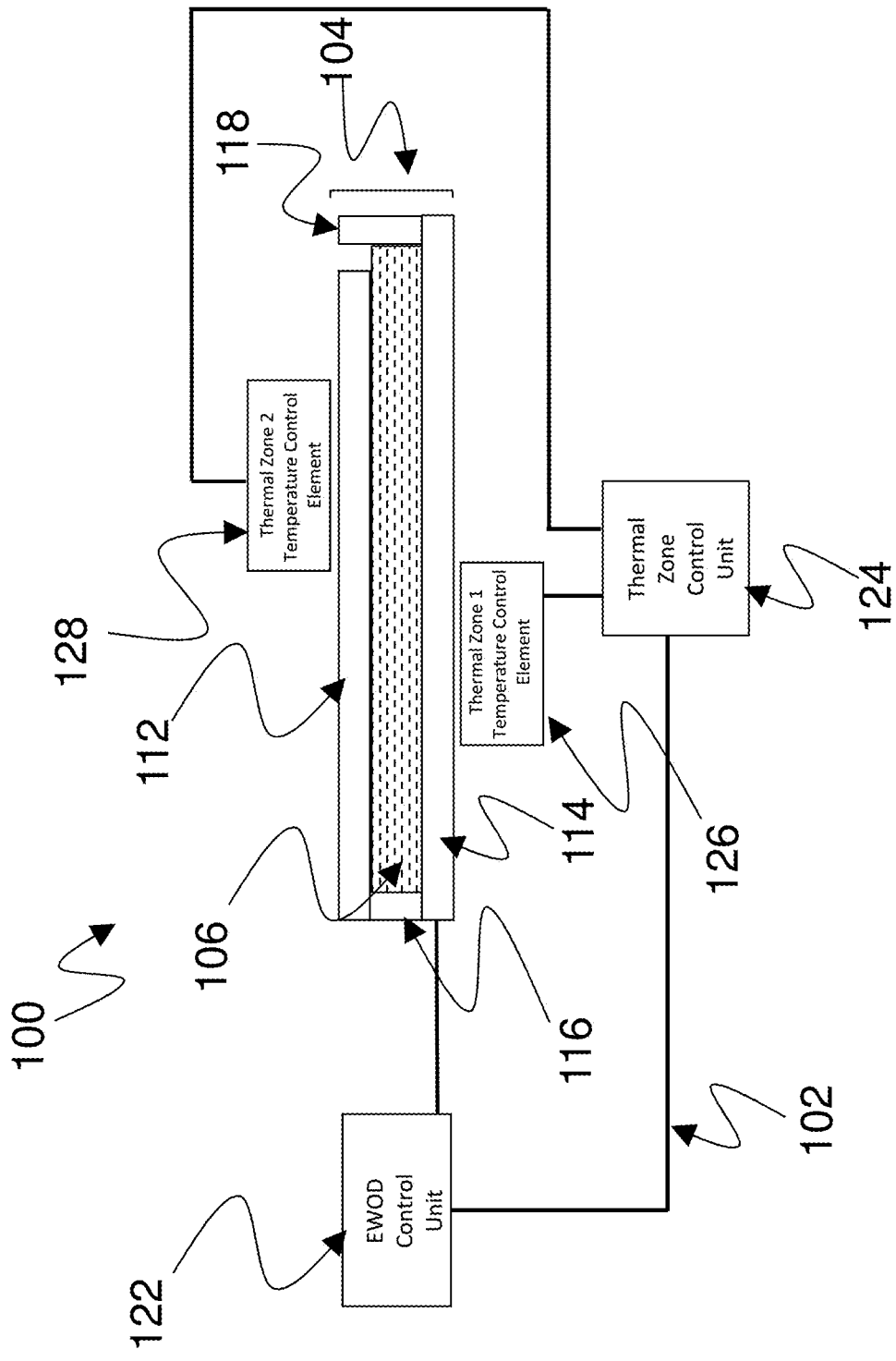

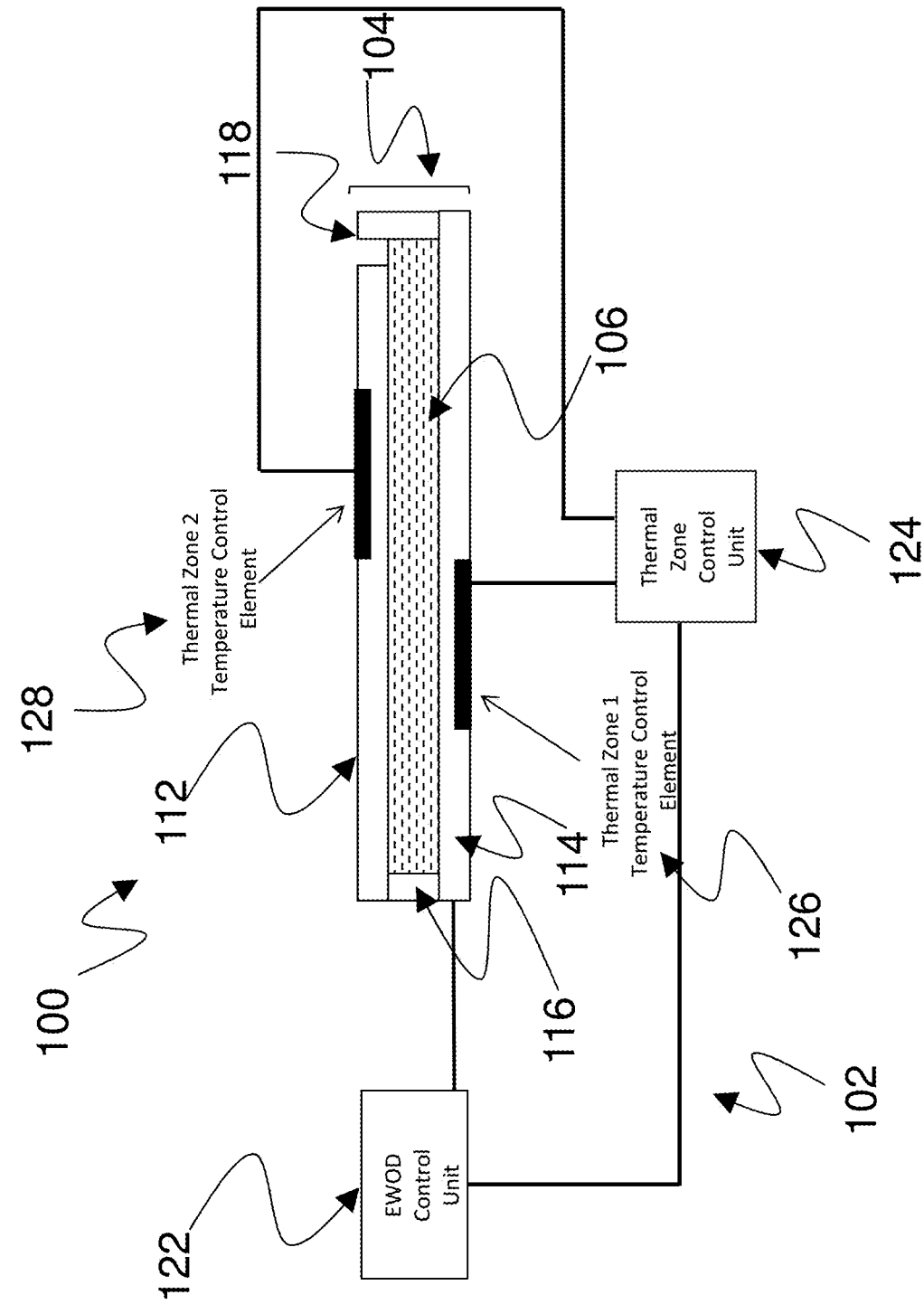

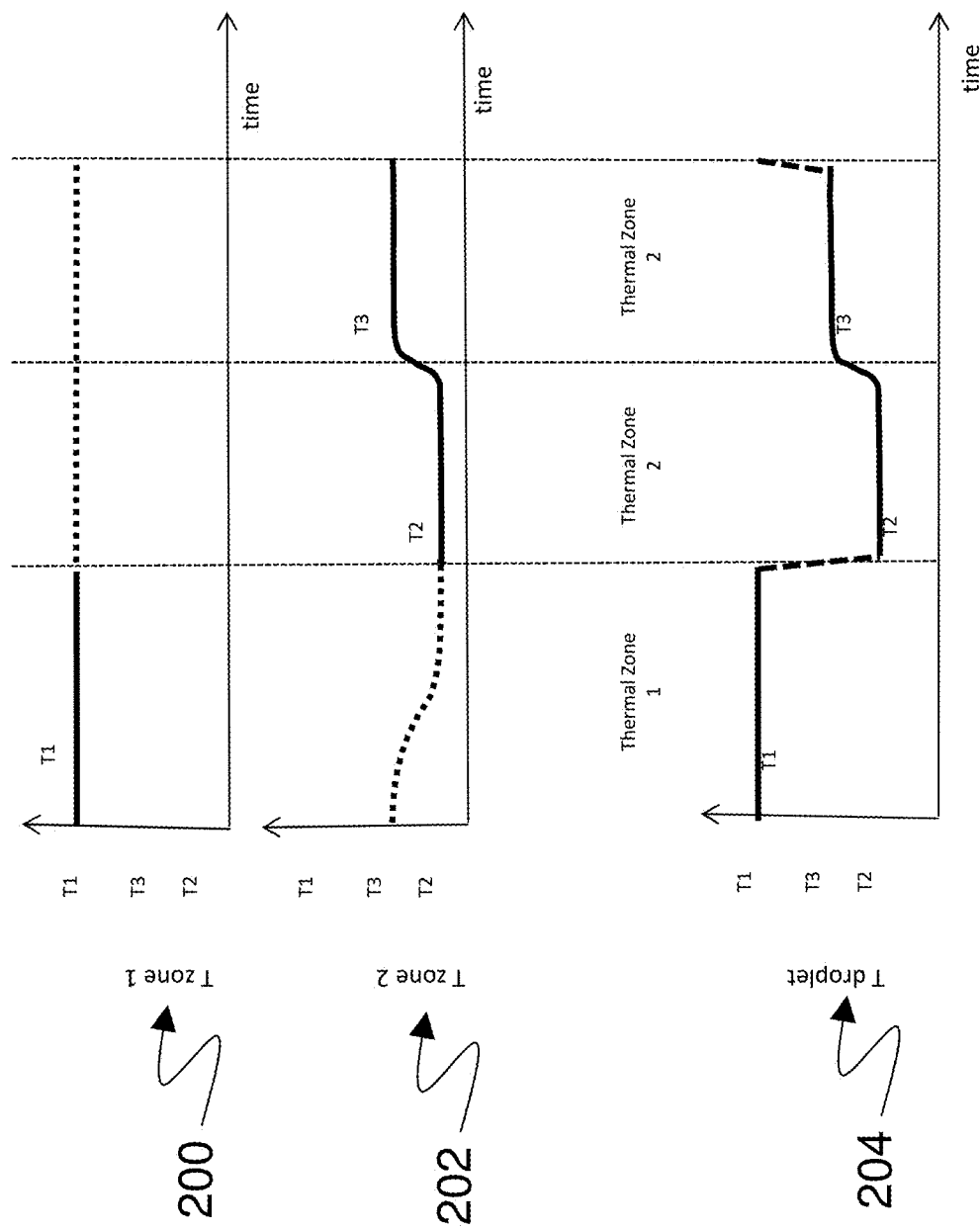

MICROFLUIDIC DEVICE WITH MULTIPLE TEMPERATURE ZONES AND ENHANCED TEMPERATURE CONTROL

TECHNICAL FIELD

The present invention relates to droplet microfluidic devices, and more specifically to Active Matrix Electrowetting-On-Dielectric (AM-EWOD) devices and structures and control methods for enhanced temperature control of multiple temperature zones in such devices.

BACKGROUND ART

Electrowetting on dielectric (EWOD) is a well-known technique for manipulating droplets of fluid by the application of an electric field. Active Matrix EWOD (AM-EWOD) refers to implementation of EWOD in an active matrix array incorporating transistors, for example by using thin film transistors (TFTs). It is thus a candidate technology for digital microfluidics for lab-on-a-chip technology. An introduction to the basic principles of the technology can be found in "Digital microfluidics: is a true lab-on-a-chip possible?", R. B. Fair, Microfluid Nanofluid (2007) 3:245-281).

FIG. 1 shows a part of a conventional EWOD device in cross section. The device includes a lower substrate 10, the uppermost layer of which is formed from a conductive material which is patterned so that a plurality of array element electrodes 12 (e.g., 12A and 12B in FIG. 1) are realized. The electrode of a given array element may be termed the element electrode 12. A liquid droplet 14, including a polar material (which is commonly also aqueous and/or ionic), is constrained in a plane between the lower substrate 10 and a top substrate 16. A suitable gap between the two substrates may be realized by means of a spacer 18, and a non-polar surround fluid 20 (e.g. oil) may be used to occupy the volume not occupied by the liquid droplet 14. An insulator layer 22 disposed upon the lower substrate 10 separates the conductive element electrodes 12A, 12B from a first hydrophobic coating 24 upon which the liquid droplet 14 sits with a contact angle 26 represented by θ. The hydrophobic coating is formed from a hydrophobic material (commonly, but not necessarily, a fluoropolymer).

On the top substrate 16 is a second hydrophobic coating 28 with which the liquid droplet 14 may come into contact. Interposed between the top substrate 16 and the second hydrophobic coating 28 is a reference electrode 30.

The contact angle θ is defined as shown in FIG. 1, and is determined by the balancing of the surface tension components between the solid-to liquid ($\gamma_{SL}$), the liquid-to non-polar surrounding fluid ($\gamma_{LG}$) and the solid to non-polar surrounding fluid ($\gamma_{SG}$) interfaces, and in the case where no voltages are applied satisfies Young's law, the equation being given by:

$$\cos\theta = \frac{\gamma_{SG} - \gamma_{SL}}{\gamma_{LG}} \qquad \text{(equation 1)}$$

In operation, voltages termed the EW drive voltages, (e.g. $V_T$, $V_0$ and $V_{00}$ in FIG. 1) may be externally applied to different electrodes (e.g. reference electrode 30, element electrodes 12, 12A and 12B, respectively). The resulting electrical forces that are set up effectively control the hydrophobicity of the hydrophobic coating 24. By arranging for different EW drive voltages (e.g. $V_0$ and $V_{00}$) to be applied to different element electrodes (e.g. 12A and 12B), the liquid droplet 14 may be moved in the lateral plane between the two substrates 10 and 16.

Example configurations and operation of EWOD devices are described in the following. U.S. Pat. No. 6,911,132 (Pamula et al., issued Jun. 28, 2005) discloses a two dimensional EWOD array to control the position and movement of droplets in two dimensions. U.S. Pat. No. 6,565,727 (Shenderov, issued May 20, 2003) further discloses methods for other droplet operations including the splitting and merging of droplets, and the mixing together of droplets of different materials. U.S. Pat. No. 7,163,612 (Sterling et al., issued Jan. 16, 2007) describes how TFT based thin film electronics may be used to control the addressing of voltage pulses to an EWOD array by using circuit arrangements very similar to those employed in AM display technologies.

The approach of U.S. Pat. No. 7,163,612 may be termed "Active Matrix Electrowetting on Dielectric" (AM-EWOD). There are several advantages in using TFT based thin film electronics to control an EWOD array, namely:

Electronic driver circuits can be integrated onto the lower substrate 10.

TFT-based thin film electronics are well suited to the AM-EWOD application. They are cheap to produce so that relatively large substrate areas can be produced at relatively low cost.

TFTs fabricated in standard processes can be designed to operate at much higher voltages than transistors fabricated in standard CMOS processes. This is significant since many EWOD technologies require electro-wetting voltages in excess of 20V to be applied.

EWOD droplet manipulation devices are a highly desirable platform for automation of chemical/biochemical reactions. Such devices may carry out chemical/biochemical reactions or reaction sequences in droplets that require complex droplet temperature profiles. Different steps of the reactions may need to be performed at different temperatures. There are many applications of EWOD devices that require the temperature of the sample/reagent droplets (and the products produced by combining them together) to be varied to facilitate the desired chemical or biochemical reaction. Many of these reaction protocols require droplets to be taken to multiple different temperatures at different times in the reaction sequence. Many reaction protocols require the droplets to be thermally cycled in time, in some cases undergoing many such thermal cycles. A significant example of a reaction protocol that requires precise temperature control in an EWOD device over many reaction cycles is droplet based nucleic acid amplification via polymerase chain reaction (PCR). PCR is a well-known reaction protocol for nucleic acid amplification.

One approach to handling multiple temperature requirements in an EWOD device is to provide multiple fixed temperature thermal zones. With such approach, conventionally a temperature control system, which usually is located external to the EWOD device, is arranged to control different parts of the EWOD device or "'zones" to be at different and fixed temperatures. Accordingly, once heated to such temperature, the temperature remains constant in time. The temperature of droplets may then be modified by moving the droplets through the device to locations having different temperatures. This approach has been used particularly for EWOD devices constructed from a material having low thermal conductivity, such as for example glass, since it is possible to realize zones of different temperatures that are relatively close together in space, as heat is not transferred so easily laterally through the substrate material of the device. Each necessary temperature for a reaction protocol, therefore, must be provided in a separate thermal zone.

As examples of such approach, U.S. Pat. No. 9,452,433B2 (Shenderov et al., issued Sep. 27, 2016) describes a device for PCR amplification of nucleic acids comprising an EWOD device for droplet manipulation and two or more reaction zones with different temperatures, which are maintained at particular temperatures. A related patent in the same patent family, U.S. Pat. No. 9,517,469B2 (Shenderov et al., issued Dec. 13, 2016) describes related methods for PCR providing at least one reaction droplet to at least two reaction zones in the electrowetting array, each reaction zone having a different temperature needed for the nucleic acid amplification reaction and moving droplets using electrowetting between these reaction zones. Again, reaction zones with different temperatures are maintained at particular temperatures.

Another approach has been to adjust or vary device temperature in time. In such approach, the temperature of the EWOD device (or in an area of the device) can be varied in time, i.e. the temperature of the whole device or some substantial portion of the device can be modified.

SUMMARY OF INVENTION

For high sample through-put and reduced cost per sample, the area of an EWOD device used for droplet processing should be maximized. EWOD devices are well suited to minimizing the volumes of samples and reagents for performing droplet manipulation protocols, e.g. for sample preparation or chemical or biochemical reactions and assays. To maximize sample throughput and/or minimize the overall cost of performing the protocol, it is desirable to make the total area of the EWOD device as small as possible, or equivalently to maximize the number of droplets that can be processed on a device (i.e., maximizing the number of reactions per area of chip per unit time). For droplet reaction protocols or reaction sequences that have complex thermal requirements optimizing droplet processing density is challenging.

Both conventional approaches of having multiple fixed temperature thermal zones, and time varying device temperature, have significant disadvantages. Having multiple fixed temperature thermal zones typically results in an inefficient use of the device area or inefficiencies in the space domain. A thermal zone of one particular temperature may only be required for occasional steps in the overall protocol, and for the rest of the time this device area is unused and effectively being wasted. This disadvantage may be particularly severe for protocols with many temperature steps, or having one or more temperature steps that are employed only for a short proportion of the overall reaction time. Reducing the number of fixed temperature zones in this approach to improve efficiency in the space domain otherwise results in non-optimized droplet temperature profiles, and this balance between number of zones versus spatial efficiency is difficult to achieve.

Alternatively, having a time variable temperature device or thermal zones, while providing more flexibility in the spatial domain, is inefficient in the time domain. Changing the temperature often requires a significant "wait time" to elapse while the temperature in the channel of the EWOD device re-equilibrates. This results in "dead time" when the protocol has to be paused, typically for many seconds or minutes, while the temperature re-equilibrates. This disadvantage may be particularly severe for EWOD devices constructed from a material that has a low thermal conductivity such as glass. However, glass and similar materials are advantageous for fabricating EWOD devices, and especially AM-EWOD devices. Accordingly, providing a suitable device with time varying temperature made out of preferred materials also is difficult to achieve.

Inefficiency in either the time or space domain has the overall result of reducing the number of droplets that can be processed on a device, i.e., reduces the number of reactions per area of chip per unit time. Accordingly, an effective device for performing a reaction protocol that requires precise temperature control in an EWOD device over many reaction cycles has not been adequately achieved.

The present invention provides enhanced control of temperature in an EWOD device so as to optimize temperature in the EWOD channel where the droplet manipulations and reactions occur. The present invention combines spatial and temporal temperature control to provide a synergistic efficiency in space and time that has not been achieved by conventional configurations. An EWOD device control system and related control methods minimize the number of thermal zones required and minimize the area occupied by such thermal zones. In addition, one or more of the different thermal zones may be varied in temperature in time. By combining spatial and temporal control of temperature in the EWOD device, a temperature profile in the droplet channel of the EWOD device is generated that is optimized for the execution of a given biochemical/chemical reaction protocol or sequence of reactions over many cycles. In this manner, the reaction protocol is not compromised and the number and size of the thermal zones may be optimized.

A microfluidic system includes a control system and an EWOD device, and optionally an AM-EWOD device in particular. The control system includes an EWOD control unit that has control electronics and CPU processing for controlling the movement of droplets on the device. The control system further includes a thermal zone control unit and at least two thermal control elements. The thermal zone control unit contains electronics and processing for controlling the temperature of the thermal control elements to generate different temperature control zones within the EWOD device. The thermal control elements may be arranged to be in thermal contact with the EWOD device, such as being arranged on either an outer surface or within the EWOD device to be in physical contact with the said surface of the EWOD device. The two or more thermal control elements may be in contact with the same surface or with opposite facing surfaces of the EWOD device.

The thermal control elements may be capable of actively heating, cooling or both heating and cooling the EWOD device as required and as determined by the thermal zone control unit in accordance with any desired reaction protocol. Heating and/or cooling may be implemented by any well-known mechanism. For example, heating may be by Joule heating or resistance heating, and cooling may be by means of the Peltier effect as are known in the art for heating and cooling. Heating and/or cooling may be applied to the outer surfaces of the EWOD device, which in turn controls the temperature in the lateral plane between the two glass substrates of the EWOD device that forms the EWOD channel. The EWOD channel defines the region of the EWOD device in which the droplets are constrained and, in effect, the temperature as controlled within the EWOD channel determines the temperature of the droplets located within said channel.

The thermal control unit is configured to control the thermal control elements to generate at least two thermal zones within the channel of the EWOD device, wherein the temperature of at least one of the thermal zones is also variable with respect to time. The temperature in the channel of the EWOD device is thus varied and controlled both spatially and temporally. During the course of a chemical/biochemical reaction protocol or sequence of reactions, droplets of a reaction mixture are moved by electrowetting between thermal zones or maintained in a given thermal zone. The temperature of a given droplet is thus a function of both its position in the channel and the time elapsed since the start of the protocol. By combining the spatial and temperature control, disadvantages of conventional configurations are eliminated, and the capacity for droplet manipulations and reactions is maximized over a substantially smaller area of an EWOD device as compared to conventional configurations.

By using multiple temperature thermal zones combined with temporal temperature control in one or more of such zones, droplets may be rapidly transitioned between different temperatures by lateral movement through the EWOD channel of the EWOD device. In addition, temporal control of one or more zones permits reassigning to different temperature values at different points during the protocol. This means that the same zone may be used for different reaction steps as different times in the protocol, separated by reaction steps being performed at other spatial zones while the variable zones are adjusted.

As a result, the inefficient use of device area common in conventional configurations having only fixed temperature zones is avoided. Once droplet(s) have completed a reaction step at a given temperature within a zone and that temperature is no longer needed for subsequent steps, the temperature in this zone may be reassigned to a different value. The physical area associated with this zone may thus be re-used for an alternative droplet operation at a different temperature and at a different time. Relatedly, inefficient use of time in conventional time varying configurations is eliminated in that there is no longer a need to wait for temperature adjustments to perform subsequent reaction steps. By efficient programming of the reaction protocol into the control system, the temperature of a given zone may be varied at a time when the droplets are "busy doing something else" in a different zone, for example performing a part of the droplet manipulation protocol or an incubation step in a different location of the EWOD device.

The result is a synergistic effect by which droplet protocols of multiple sequenced reactions may be performed with enhanced efficiency both in time and space, such that more droplet processing steps may be performed in a given time and in a smaller device area as compared to conventional configurations. The benefits of the present invention are particularly appreciable for devices constructed from a preferred substrate material of low thermal conductivity, such as glass or like materials. The low thermal conductivity means the thermal zones of the EWOD channel can be close together in space. Using a glass substrate, EW electrode sizes are typically smaller than when using other substrate materials (e.g. Printed Circuit Board PCB). Hence, the glass EWOD device may operate with smaller droplets and be more spatially efficient. Efficient use of the device area from a thermal point of view, and thus full realization of efficiency in an overall smaller device, is achieved.

Consequently, unexpected and enhanced results are achieved particularly in connection with EWOD devices employing glass substrates, which is preferred for a high-quality AM-EWOD device. Because of the cost associated with fabricating a TFT backplane, reducing cost by reducing chip area is a synergistic advantage achieved by the present invention. AM-EWOD devices are preferably constructed with glass substrates, since this is the standard substrate material for displays and therefore the substrate material available in AM-EWOD manufacturing factories. Furthermore, AM-EWOD devices, having a very large number of array elements and a high level of configurability, are particularly well-suited to performing complex droplet manipulation protocols such as for example PCR. It is such high complexity droplet manipulation protocols that often require steps at a range of different temperatures, and thus particularly leverage the advantages of the present invention.

These and further features of the present invention will be apparent with reference to the following description and attached drawings. In the description and drawings, particular embodiments of the invention have been disclosed in detail as being indicative of some of the ways in which the principles of the invention may be employed, but it is understood that the invention is not limited correspondingly in scope. Rather, the invention includes all changes, modifications and equivalents coming within the spirit and terms of the claims appended hereto. Features that are described and/or illustrated with respect to one embodiment may be used in the same way or in a similar way in one or more other embodiments and/or in combination with or instead of the features of the other embodiments.

BRIEF DESCRIPTION OF DRAWINGS

FIG. 5A is a drawing depicting a circuit representation of the electrical load presented at the element electrode when a liquid droplet is present.

FIG. 5B is a drawing depicting a circuit representation of the electrical load presented at the element electrode when no liquid droplet is present.

FIG. 6 is a drawing depicting an exemplary arrangement of thin film electronics in the exemplary AM-EWOD device of FIG. 3 in accordance with embodiments of the present invention.

FIG. 7 is a drawing depicting an exemplary arrangement of the array element circuit in accordance with embodiments of the present invention.

FIG. 9 is a drawing depicting the microfluidic system of FIG. 8 showing an example location of a liquid droplet within the EWOD channel.

FIG. 10A, FIG. 10B, FIG. 10C, FIG. 10D, and FIG. 10E are drawings depicting the microfluid system of FIG. 8 showing various alternative configurations of positioning of the thermal control elements.

FIG. 11 is a graphical drawing depicting exemplary temperature/time profiles for first and second thermal zones, and the resultant temperature/time profile for a liquid droplet as it is moved by electrowetting between the two thermal zones.

DESCRIPTION OF EMBODIMENTS

Figure 1:
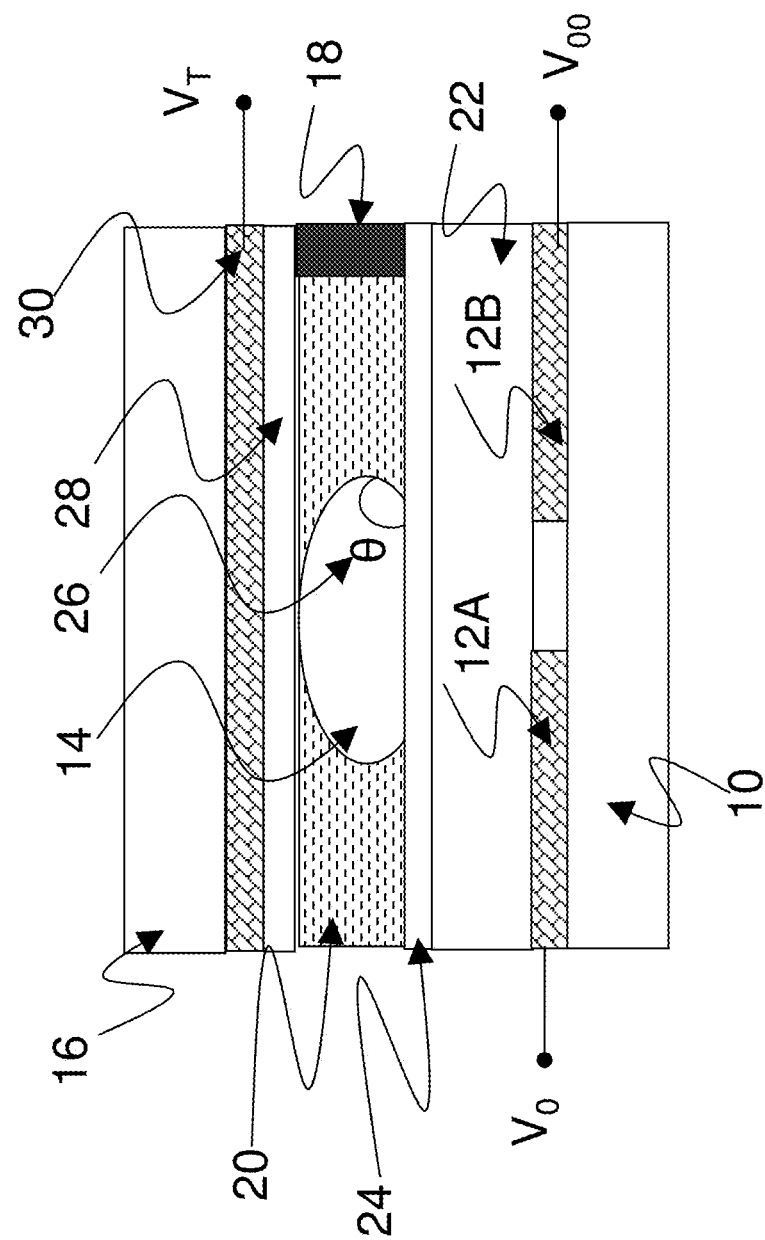
FIG. 1 is a drawing depicting a conventional EWOD device in cross-section.

Embodiments of the present invention will now be described with reference to the drawings, wherein like reference numerals are used to refer to like elements throughout. It will be understood that the figures are not necessarily to scale.

Figure 2:
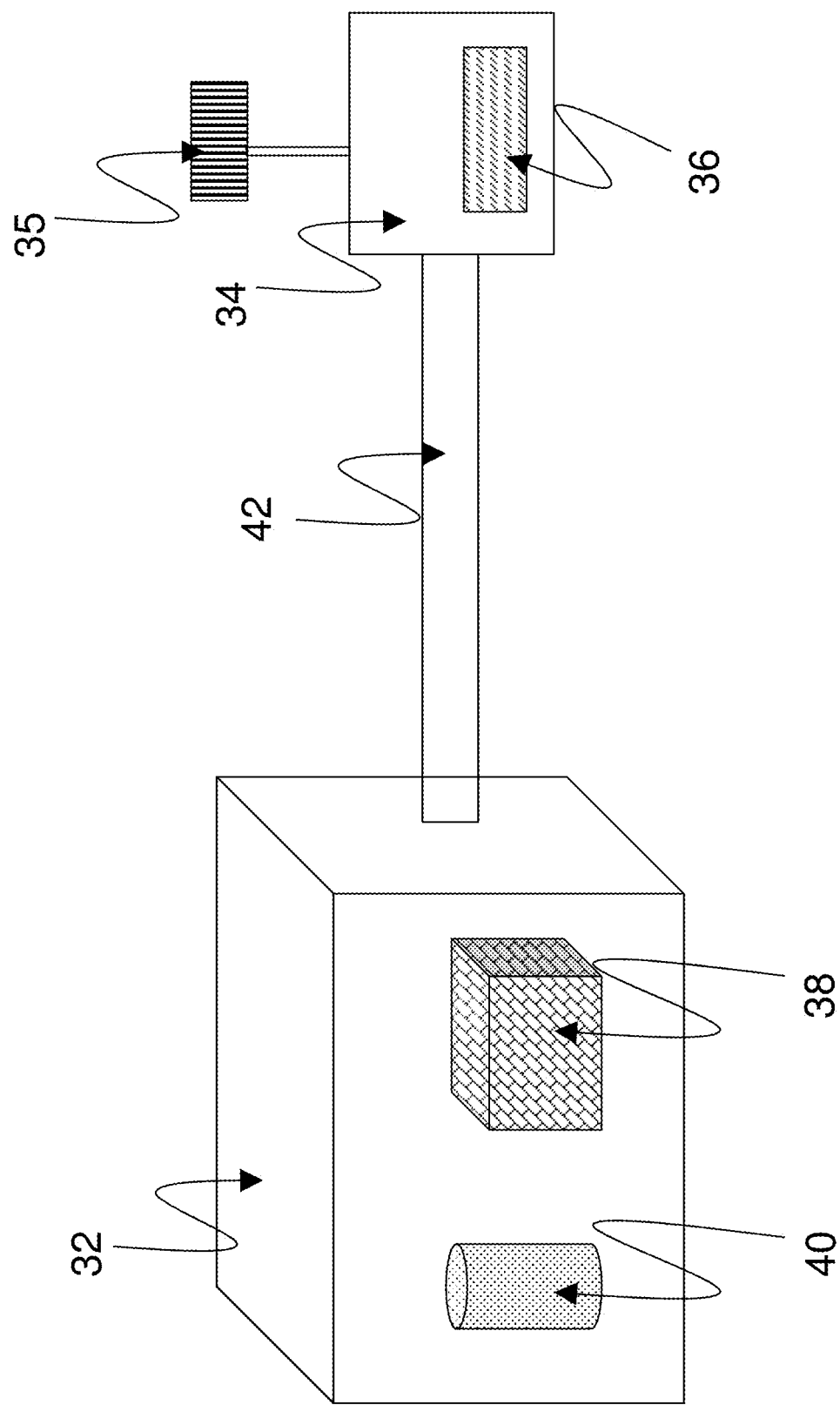
FIG. 2 is a drawing depicting an exemplary EWOD based microfluidic system according to embodiments of the present invention.

FIG. 2 is a drawing depicting an exemplary EWOD based microfluidic system according to embodiments of the present invention. In the example of FIG. 2, the measurement system includes a reader 32 and a cartridge 34. The cartridge 34 may contain a microfluidic device, such as an EWOD or AM-EWOD device 36, as well as (not shown) fluid input ports into the device and an electrical connection as are conventional. The fluid input ports may perform the function of inputting fluid into the AM-EWOD device 36 and generating droplets within the device, for example by dispensing from input reservoirs as controlled by electro-wetting. As further detailed below, the microfluidic device includes an electrode array configured to receive the inputted fluid droplets.

The microfluidic system further may include a control system configured to control actuation voltages applied to the electrode array of the microfluidic device to perform manipulation operations to the fluid droplets. For example, the reader 32 may contain such a control system configured as control electronics 38 and a storage device 40 that may store any application software any data associated with the system. The control electronics 38 may include suitable circuitry and/or processing devices that are configured to carry out various control operations relating to control of the AM-EWOD device 36, such as a CPU, microcontroller or microprocessor.

Among their functions, to implement the features of the present invention, the control electronics may comprise a part of the overall control system that may execute program code embodied as a control application within the storage device 40. It will be apparent to a person having ordinary skill in the art of computer programming, and specifically in application programming for electronic control devices, how to program the control system to operate and carry out logical functions associated with the stored control application. Accordingly, details as to specific programming code have been left out for the sake of brevity. The storage device 40 may be configured as a non-transitory computer readable medium, such as random access memory (RAM), a read-only memory (ROM), an erasable programmable read-only memory (EPROM or Flash memory), or any other suitable medium. Also, while the code may be executed by control electronics 38 in accordance with an exemplary embodiment, such control system functionality could also be carried out via dedicated hardware, firmware, software, or combinations thereof, without departing from the scope of the invention.

The control system may be configured to perform some or all of the following functions:
Define the appropriate timing signals to manipulate liquid droplets on the AM-EWOD device 36.
Interpret input data representative of sensor information measured by a sensor or sensor circuitry associated with the AM-EWOD device 36, including computing the locations, sizes, centroids and perimeters of liquid droplets on the AM-EWOD device 36.
Use calculated sensor data to define the appropriate timing signals to manipulate liquid droplets on the AM-EWOD device 36, i.e. acting in a feedback mode.
Provide for implementation of a graphical user interface (GUI) whereby the user may program commands such as droplet operations (e.g. move a droplet), assay operations (e.g. perform an assay), and the GUI may report the results of such operations to the user.
In accordance with embodiments of the present invention, and as further detailed below, the control system may include a thermal control unit configured to control temperature of the EWOD device within the EWOD channel as is suitable for a given reaction protocol.

In the example of FIG. 2, an external sensor module 35 may be provided for sensing droplet properties. For example, optical sensors as are known in the art may be employed as external sensors for sensing droplet properties. Suitable optical sensors include camera devices, light sensors, charged coupled devices (CCDs) and similar image sensors, and the like. A sensor alternatively may be configured as internal sensor circuitry incorporated as part of the drive circuitry in each array element. Such sensor circuitry may sense droplet properties by the detection of an electrical property at the array element, such as impedance or capacitance.

The control system, such as via the control electronics 38, may supply and control the actuation voltages applied to the electrode array of the microfluidics device 36, such as required voltage and timing signals to perform droplet manipulation operations and sense liquid droplets on the AM-EWOD device 36. The control electronics further may execute the application software to generate and output control voltages for droplet sensing and performing sensing operations. The reader 32 and cartridge 34 may be electrically connected together while in use, for example by a cable of connecting wires 42, although various other methods (e.g. wireless connection) of providing electrical communication may be used as are known to those of ordinary skill in the art.

Figure 3:
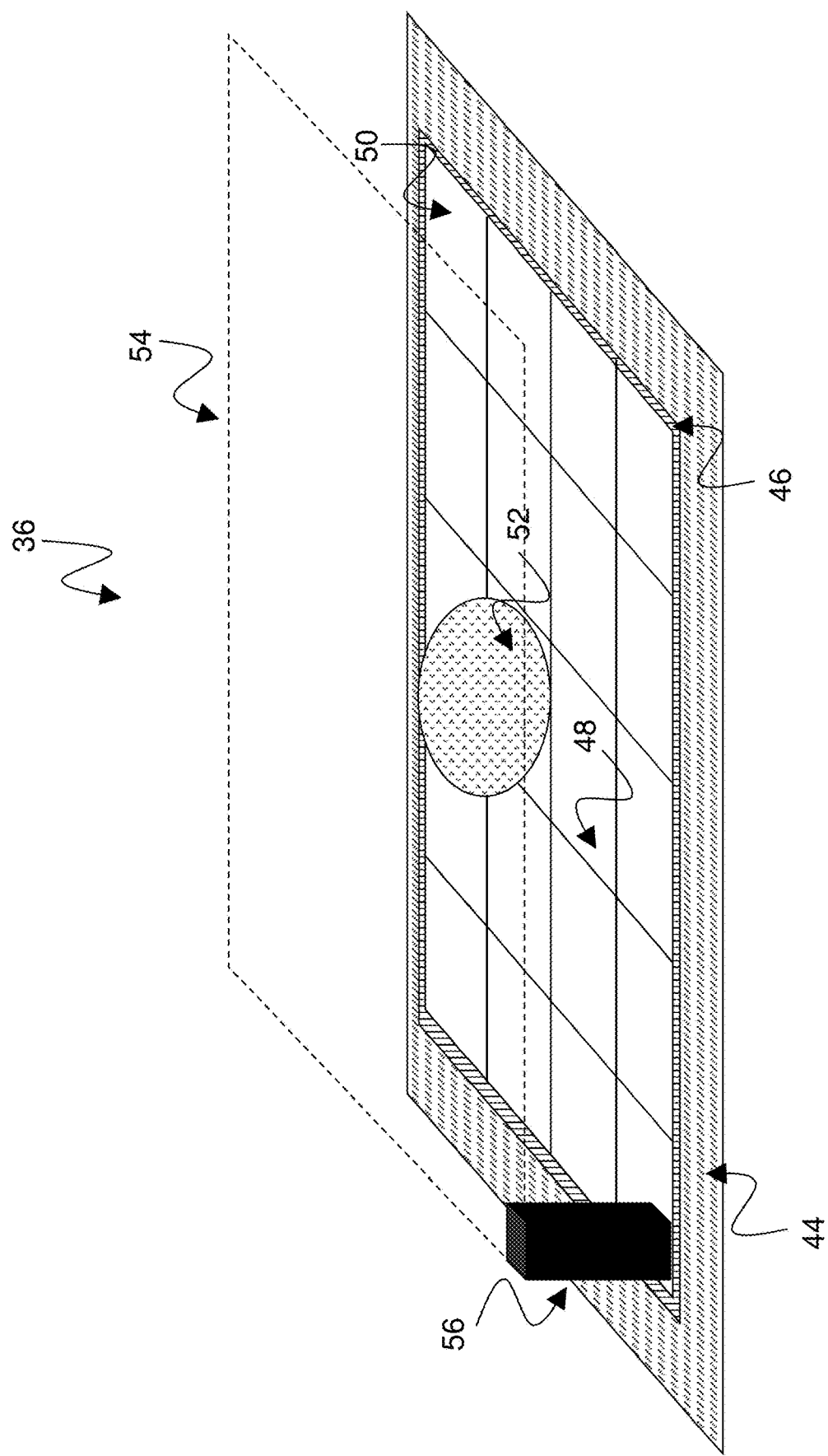
FIG. 3 is a drawing depicting an exemplary AM-EWOD device in schematic perspective in accordance with embodiments of the present invention.

FIG. 3 is a drawing depicting additional details of the exemplary AM-EWOD device 36 in schematic perspective in accordance with embodiments of the present invention. The AM-EWOD device 36 has a lower substrate 44 with thin film electronics 46 disposed upon the lower substrate 44. The thin film electronics 46 are arranged to drive array element electrodes 48. A plurality of array element electrodes 48 are arranged in an electrode or element array 50, having X by Y array elements where X and Y may be any integer. A liquid droplet 52 which may include any polar liquid and which typically may be aqueous, is enclosed between the lower substrate 44 and a top substrate 54 separated by a spacer 56, although it will be appreciated that multiple liquid droplets 52 can be present.

Figure 4:
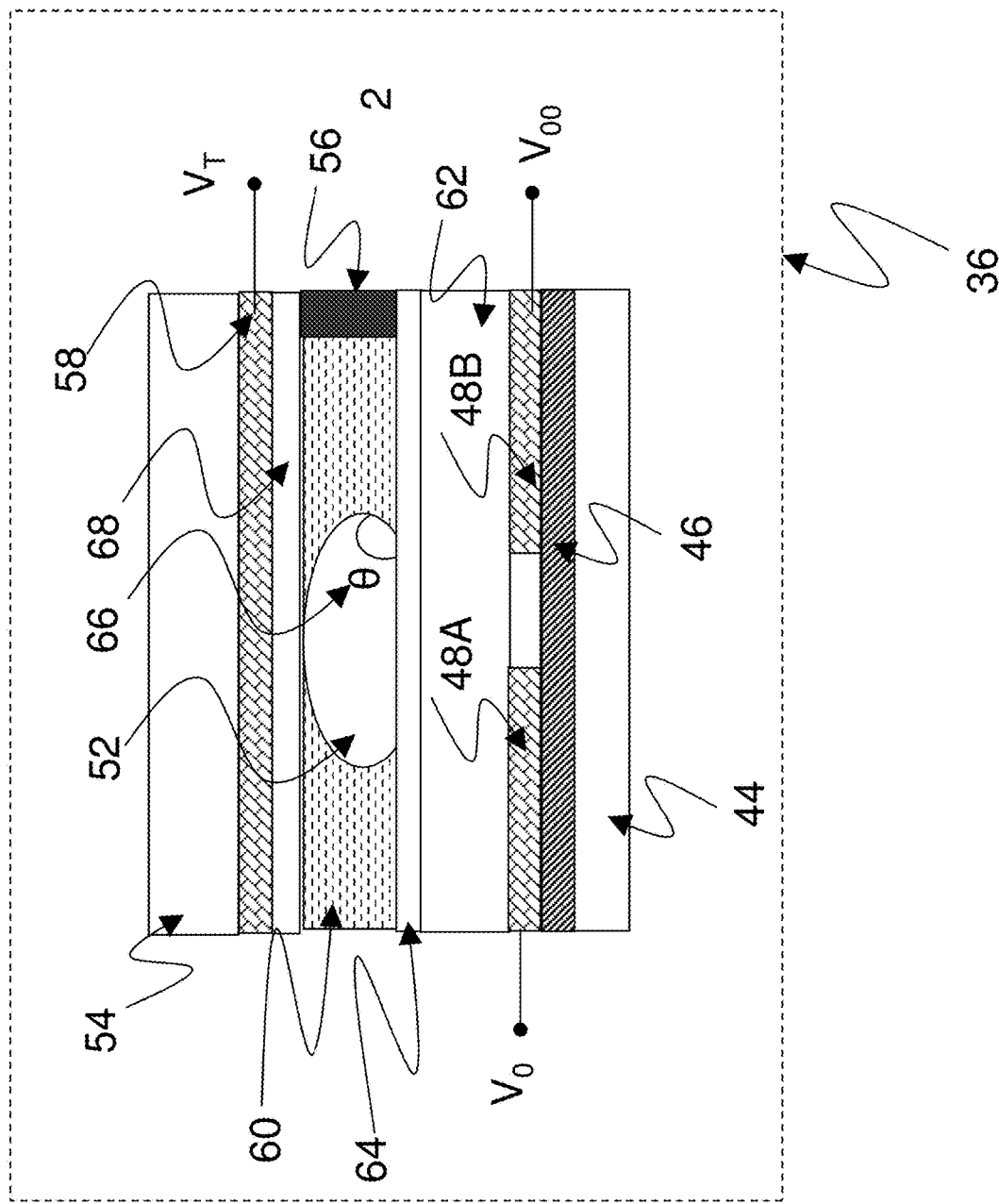
FIG. 4 is a drawing depicting a cross section through some of the array elements of the exemplary AM-EWOD device of FIG. 3.

FIG. 4 is a drawing depicting a cross section through some of the array elements of the exemplary AM-EWOD 36 device of FIG. 3. In the portion of the AM-EWOD device depicted in FIG. 4, the device includes a pair of the array element electrodes 48A and 48B that are shown in cross section that may be utilized in the electrode or element array 50 of the AM-EWOD device 36 of FIG. 3. The device configuration is similar to the conventional configuration shown in FIG. 1, with the AM-EWOD device 36 further incorporating the thin-film electronics 46 disposed on the lower substrate 44, which is separated from the upper substrate 54 by the spacer 56. The uppermost layer of the lower substrate 44 (which may be considered a part of the thin film electronics layer 46) is patterned so that a plurality of the array element electrodes 48 (e.g. specific examples of array element electrodes are 48A and 48B in FIG. 4) are realized. The term element electrode 48 may be taken in what follows to refer both to the physical electrode structure 48 associated with a particular array element, and also to the node of an electrical circuit directly connected to this physical structure. A reference electrode 58 is shown in FIG. 4 disposed upon the top substrate 54, but the reference electrode alternatively may be disposed upon the lower substrate 44 to realize an in-plane reference electrode geometry. The term reference electrode 58 may also be taken in what follows to refer to both or either of the physical electrode structure and also to the node of an electrical circuit directly connected to this physical structure.

Also similarly to the conventional structure of FIG. 1, in the AM-EWOD device 36, a non-polar fluid 60 (e.g. oil) may be used to occupy the volume not occupied by the liquid droplet 52. An insulator layer 62 may be disposed upon the lower substrate 44 that separates the conductive element electrodes 48A and 48B from a first hydrophobic coating 64 upon which the liquid droplet 52 sits with a contact angle 66 represented by θ. The hydrophobic coating is formed from a hydrophobic material (commonly, but not necessarily, a fluoropolymer). On the top substrate 54 is a second hydrophobic coating 68 with which the liquid droplet 52 may come into contact. The reference electrode 58 is interposed between the top substrate 54 and the second hydrophobic coating 68.

FIG. 5A shows a circuit representation of the electrical load 70A between the element electrode 48 and the reference electrode 58 in the case where a liquid droplet 52 is present. The liquid droplet 52 can usually be modeled as a resistor and capacitor in parallel. Typically, the resistance of the droplet will be relatively low (e.g. if the droplet contains ions) and the capacitance of the droplet will be relatively high (e.g. because the relative permittivity of polar liquids is relatively high, e.g. ~80 if the liquid droplet is aqueous). In many situations the droplet resistance is relatively small, such that at the frequencies of interest for electro-wetting, the liquid droplet 52 may function effectively as an electrical short circuit. The hydrophobic coatings 64 and 68 have electrical characteristics that may be modelled as capacitors, and the insulator 62 may also be modelled as a capacitor. The overall impedance between the element electrode 48 and the reference electrode 58 may be approximated by a capacitor whose value is typically dominated by the contribution of the insulator 62 and hydrophobic coatings 64 and 68 contributions, and which for typical layer thicknesses and materials may be on the order of a pico-Farad in value.

FIG. 5B shows a circuit representation of the electrical load 70B between the element electrode 48 and the reference electrode 58 in the case where no liquid droplet is present. In this case the liquid droplet components are replaced by a capacitor representing the capacitance of the non-polar fluid 60 which occupies the space between the top and lower substrates. In this case the overall impedance between the element electrode 48 and the reference electrode 58 may be approximated by a capacitor whose value is dominated by the capacitance of the non-polar fluid and which is typically small, of the order of femto-Farads.

For the purposes of driving and sensing the array elements, the electrical load 70A/70B overall functions in effect as a capacitor, whose value depends on whether a liquid droplet 52 is present or not at a given element electrode 48. In the case where a droplet is present, the capacitance is relatively high (typically of order pico-Farads), whereas if there is no liquid droplet present the capacitance is low (typically of order femto-Farads). If a droplet partially covers a given electrode 48 then the capacitance may approximately represent the extent of coverage of the element electrode 48 by the liquid droplet 52.

FIG. 6 is a drawing depicting an exemplary arrangement of thin film electronics 46 in the exemplary AM-EWOD device 36 of FIG. 3 in accordance with embodiments of the present invention. The thin film electronics 46 is located upon the lower substrate 44. Each array element 51 of the array of elements 50 contains an array element circuit 72 for controlling the electrode potential of a corresponding element electrode 48. Integrated row driver 74 and column driver 76 circuits are also implemented in thin film electronics 46 to supply control signals to the array element circuit 72. The array element circuit 72 may also contain a sensing capability for detecting the presence or absence of a liquid droplet in the location of the array element. Integrated sensor row addressing 78 and column detection circuits 80 may further be implemented in thin film electronics for the addressing and readout of the sensor circuitry in each array element.

A serial interface 82 may also be provided to process a serial input data stream and facilitate the programming of the required voltages to the element electrodes 48 in the array 50. A voltage supply interface 84 provides the corresponding supply voltages, top substrate drive voltages, and other requisite voltage inputs as further described herein. A number of connecting wires 86 between the lower substrate 44 and external control electronics, power supplies and any other components can be made relatively few, even for large array sizes. Optionally, the serial data input may be partially parallelized. For example, if two data input lines are used the first may supply data for columns 1 to X/2, and the second for columns (1+X/2) to M with minor modifications to the column driver circuits 76. In this way the rate at which data can be programmed to the array is increased, which is a standard technique used in Liquid Crystal Display driving circuitry.

Generally, an exemplary AM-EWOD device 36 that includes thin film electronics 46 may be configured as follows. The AM-EWOD device 36 includes the reference electrode 58 mentioned above (which, optionally, could be an in-plane reference electrode) and a plurality of individual array elements 51 on the array of elements 50, each array element 51 including an array element electrode 48 and array element circuitry 72. Relatedly, the AM-EWOD device 36 may be configured to perform a method of actuating the array elements to manipulate liquid droplets on the array by controlling an electro-wetting voltage to be applied to a plurality of array elements. The applied voltages may be provided by operation of the control system described as to FIG. 2, including the control electronics 38 and applications and data stored on the storage device 40. The electro-wetting voltage at each array element 51 is defined by a potential difference between the array element electrode 48 and the reference electrode 58. The method of controlling the electro-wetting voltage at a given array element typically includes the steps of supplying a voltage to the array element electrode 48, and supplying a voltage to the reference electrode 58, by operation of the control system.

FIG. 7 is a drawing depicting an exemplary arrangement of the array element circuit 72 present in each array element 51, in accordance with embodiments of the present invention. The array element circuit 72 may contain an actuation circuit 88, having inputs ENABLE, DATA and ACTUATE, and an output which is connected to an element electrode 48. The array element circuit 72 also may contain a droplet sensing circuit 90, which may be in electrical communication with the element electrode 48. Typically, the read-out of the droplet sensing circuit 90 may be controlled by one or more addressing lines (e.g. RW) that may be common to elements in the same row of the array, and may also have one or more outputs, e.g. OUT, which may be common to all elements in the same column of the array.

The array element circuit 72 may typically perform the functions of:
  (i) Selectively actuating the element electrode 48 by supplying a voltage to the array element electrode. Accordingly, any liquid droplet present at the array element 51 may be actuated or de-actuated by the electro-wetting effect.
  (ii) Sensing the presence or absence of a liquid droplet at the location of the array element 51. The means of sensing may be capacitive, optical, thermal or some other means. Capacitive sensing may be employed conveniently and effectively using an impedance sensor circuit as part of the array element circuitry.

Exemplary configurations of array element circuits 72 including impedance sensor circuitry are known in the art, and for example are described in detail in U.S. Pat. No. 8,653,832 referenced in the background art section, and commonly assigned UK application GB1500261.1, both of which are incorporated here by reference. These patent documents include descriptions of how the droplet may be actuated (by means of electro-wetting) and how the droplet may be sensed by capacitive or impedance sensing means. Typically, capacitive and impedance sensing may be analogue and may be performed simultaneously, or near simultaneously, at every element in the array. By processing the returned information from such a sensor (for example in the application software in the storage device 40 of the reader 32), the control system described above can determine in real-time, or almost real-time the position, size, centroid and perimeter of each liquid droplet present in the array of elements 50. As referenced in connection with FIG. 2, an alternative to sensor circuitry is to provide an external sensor (e.g., sensor 35), such as an optical sensor that can be used to sense droplet properties.

The present invention provides enhanced control of temperature in an EWOD device to optimize temperature in the EWOD channel where the droplet manipulations and reactions occur. The present invention combines spatial and temporal temperature control to provide a synergistic efficiency in space and time that has not been achieved by conventional configurations. An EWOD device control system and related control methods minimize the number of thermal zones required and minimize the area occupied by such thermal zones. In addition, one or more of the different thermal zones may be varied in temperature in time. By combining spatial and temporal control of temperature in the EWOD device, a temperature profile in the droplet channel of the EWOD device is generated that is optimized for the execution of a given biochemical/chemical reaction or sequence of reactions over many cycles. In this manner, the reaction protocol is performed efficiently with the number and size of the thermal zones being optimized.

Generally, therefore, an aspect of the invention is a microfluidic system configured for enhanced temperature control by combining spatial and temporal temperature control. In exemplary embodiments, the microfluidic system includes an electro-wetting on dielectric (EWOD) device comprising an element array configured to receive one or more liquid droplets, the element array comprising a plurality of individual array elements; a control system configured to control actuation voltages applied to the element array to perform manipulation operations as to the liquid droplets; and a plurality of thermal control elements located at different spatial locations along the EWOD device, at least one of the thermal control elements being variable in temperature with respect to time. The control system includes a thermal control unit configured to control temperatures of the plurality of thermal control elements to generate a plurality of thermal zones located at different spatial locations along the EWOD device, at least one of the thermal zones being variable in temperature with respect to time.

Figure 8:
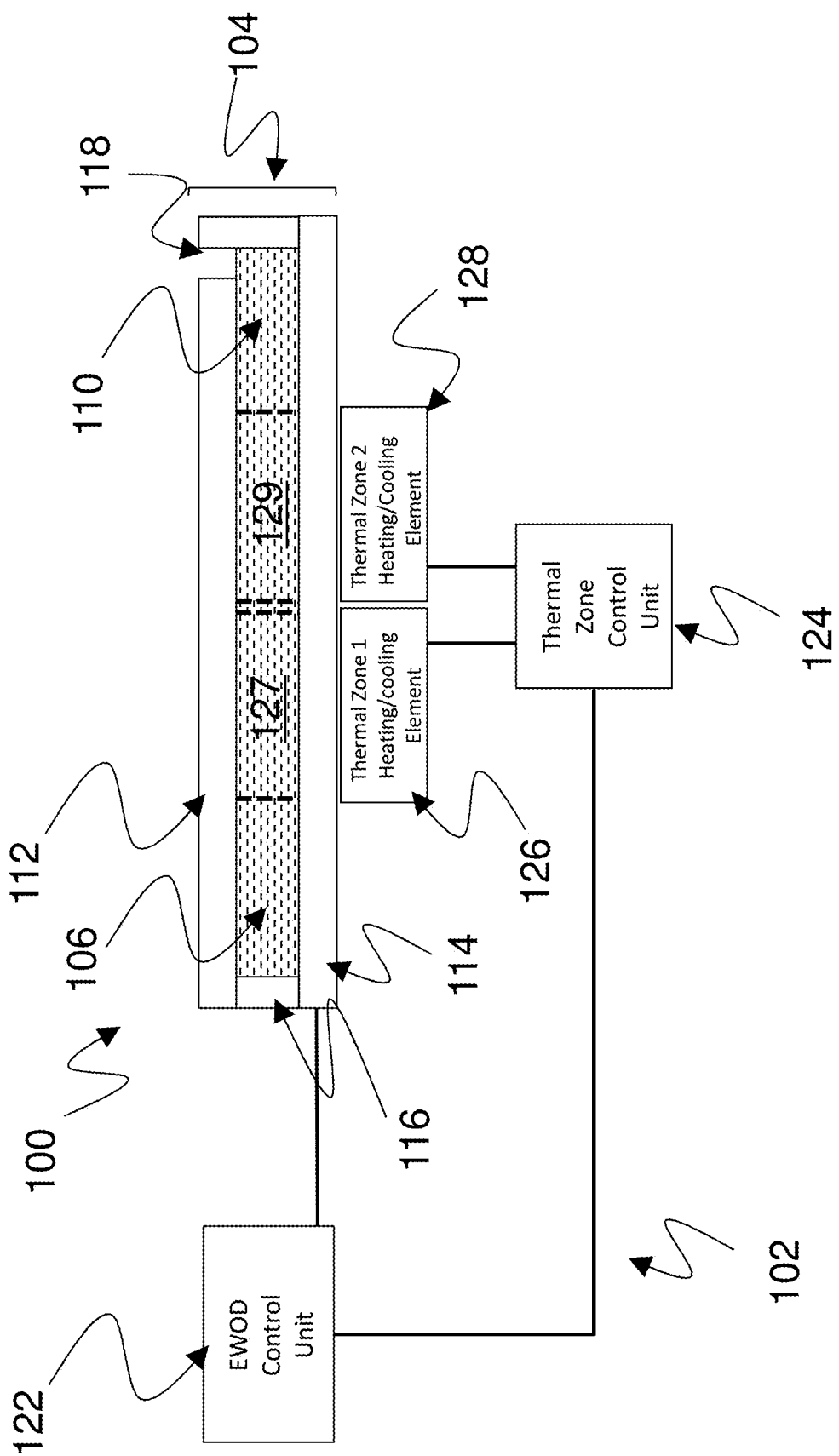
FIG. 8 is a drawing depicting an exemplary microfluidic system in accordance with embodiments of the present invention including thermal control elements.

FIG. 8 is a drawing depicting an exemplary microfluidic system 100 in accordance with embodiments of the present invention, which includes a control system 102 and an EWOD device 104 (which in particular may be an AM-EWOD device) that defines an EWOD channel 106. FIG. 9 is a drawing depicting the microfluidic system 100 of FIG. 8 showing an example location of a liquid droplet 108 within the EWOD channel 106.

Generally, the microfluidic system includes a controller system and EWOD (or AM-EWOD) device. The controller system includes a thermal control unit configured to generate at least two thermal zones within the channel of the EWOD device, wherein the temperature of at least one of the thermal zones is controlled dynamically (i.e. time varied). An EWOD control unit operates to apply actuation voltages to array elements of the EWOD device to move droplets between the two thermal zones. The thermal zones are created by thermal control elements, controlled by a thermal zone control unit.

In exemplary embodiments, one or more of the following features may be incorporated into the microfluidic system. The thermal control elements may each be configured to heat, cool, or both heat and cool the associated thermal zone in the EWOD device. The thermal control elements may be in thermal communication with either the top or bottom outer faces of the EWOD device (the same or opposite faces). In a case where one or more thermal control elements are configured to apply heat (e.g. by resistive Joule heating), the thermal zone control element may be integrated in the EWOD device. An example of integrated thermal control elements is described, for example, in Applicant's U.S. application Ser. No. 13/092,194, filed Apr. 22, 2011, which is incorporated herein by reference. A temperature sensing element as known in the art may be incorporated at one or more positions in the system structure. Such temperature sensing elements may be components of the thermal control elements, and may include one or more of external temperature sensors (e.g. thermistors) attached to an outer surface of the EWOD device, temperature sensors integrated into the EWOD device, e.g. as described in Applicant's U.S. application Ser. No. 12/772,245 filed May 15, 2010. (incorporated herein by reference), which may for example be incorporated into the array element of the AM-EWOD device, or a thermal control system based on proportional-integral-derivative (PID) control methods, or incorporated into the thermal zone control unit. The microfluidic system may be arranged to implement any droplet manipulation protocols requiring droplets to be heated and/or cooled to at least two temperatures as part of the droplet manipulation protocol.

Referring to FIGS. 8-9, a non-polar fluid 110 (e.g. oil) may be used to occupy the volume not occupied by the liquid droplet 108. The EWOD device may include a first (top) substrate assembly 112 and a second (bottom) substrate assembly 114 separated by a spacer 116, which define the EWOD channel 106. For simplicity of illustration of pertinent features, the individual layers of the EWOD device components are omitted. Accordingly, the first and second substrate assemblies may include the associated substrates, insulating layers, electrode layers, and related structures that form the EWOD device, such as for example the various components described with respect to FIGS. 3-7. FIGS. 8 and 9 also show a representative fluid input structure 118 for input of fluid into the EWOD channel. Various configurations of the input structure are known in the art, and therefore any suitable input structure may be employed.

As referenced above, the microfluidic system 100 further includes a control system 102. The control system 102 may be configured comparably as the control system described in connection with FIG. 2, including control electronics that may execute program code embodied as a control application incorporated within a non-transitory computer readable medium or storage device. The control system 102 may include an EWOD control unit 122 that has control electronics and CPU processing devices for controlling the movement of droplets on the EWOD device by the control of actuation voltages applied to the array elements of the EWOD device. The control system 102 further includes a thermal zone control unit 124 and a plurality of thermal control elements. In the depicted example, two thermal control elements 126 and 128 are shown positioned at different spatial locations along the EWOD device. It will be appreciated that any suitable number of a plurality of thermal control elements may be employed in a given device as may be suitable for particular microfluidic operations. The thermal zone control unit 124, similarly as the EWOD control unit 122, contains control electronics and CPU or processing devices, for controlling the temperature of the thermal control elements to generate different temperature control zones within the EWOD device. The control electronics of the thermal zone control unit likewise may similarly execute program code embodied as a thermal control application incorporated within a non-transitory computer readable medium or storage device within the thermal zone control unit.

The thermal control elements 126 and 128 may be capable of actively heating, cooling, or both heating and cooling the EWOD device as required and as determined by the thermal zone control unit 124 in accordance with any desired reaction protocol. Heating and/or cooling may be implemented by any well-known mechanism. For example, heating may be by Joule heating or resistance heating, and cooling may be by means of the Peltier effect as are known in the art for heating and cooling. A region of the EWOD channel 106 within the EWOD device whose temperature is controlled by one of the thermal control elements is referred to herein as a thermal zone. In FIGS. 8 and 9, for example, the first thermal control element 126 is operable to control the temperature of a first thermal zone 127 within the EWOD channel, and the second thermal control element 128 is operable to control the temperature of a second thermal zone 129 within the EWOD channel. Accordingly, the first and second thermal zones 127 and 129 are located at different spatial locations along the EWOD device based on corresponding locations of the thermal control elements. Again, any suitable number of a plurality of thermal control elements may be employed, which would control temperature in a corresponding number of thermal zones located at different spatial locations along the EWOD device.

A liquid droplet assumes a temperature of any thermal zone in which the liquid droplet is located. Because of the minute size of the droplet, rapid temperature equalization occurs as between the liquid droplet and the thermal zone. In the example of FIG. 9, the liquid droplet 108 is located in the first thermal zone 127, and thus would assume the temperature of the first thermal zone 127 as controlled by the first thermal control element 126. By application of appropriate actuation voltages, the liquid droplet 108 may be moved to the second thermal zone 129, and thus would then assume the temperature of the second thermal zone 129 as controlled by the second thermal control element 128.

The EWOD control unit 122 applies actuation voltages to the array elements of the EWOD device to move liquid droplets from one thermal zone to another thermal zone. The thermal zone control unit 124 and EWOD control unit 122 are organized to work together to configure dynamically controlled thermal zones which may vary the temperature in the channel in accordance with the locations of liquid droplets within the channel of the EWOD device. The position of liquid droplets in the EWOD channel may be read out with droplet position sensors (e.g., using the external sensor 35 of FIG. 3 or the droplet sensing circuit 90 of FIG. 7 based on sensing droplet impedance) which may be integrated into the EWOD droplet manipulation device. By combining spatial and temporal control of temperature in the channel of the EWOD device, the temperature profile required for the execution of a given biochemical/chemical reaction or sequence of reactions is optimized, and in turn the number and size of the thermal zones are optimized. The inclusion of the droplet position sensor(s) further enhances the system since feedback control of the droplet position may be used to determine the time at which changes to the temperature of thermal zones are implemented.

The thermal control elements 126 and 128 may be arranged to be in thermal contact with one of the substrate layers of the EWOD device, such as being arranged on either an outer surface or internally as part of the substrate layers of the EWOD device. In the example of FIGS. 8 and 9, the thermal control elements are both located on the outer surface of the second (bottom) substrate 114.

Figure 10A:
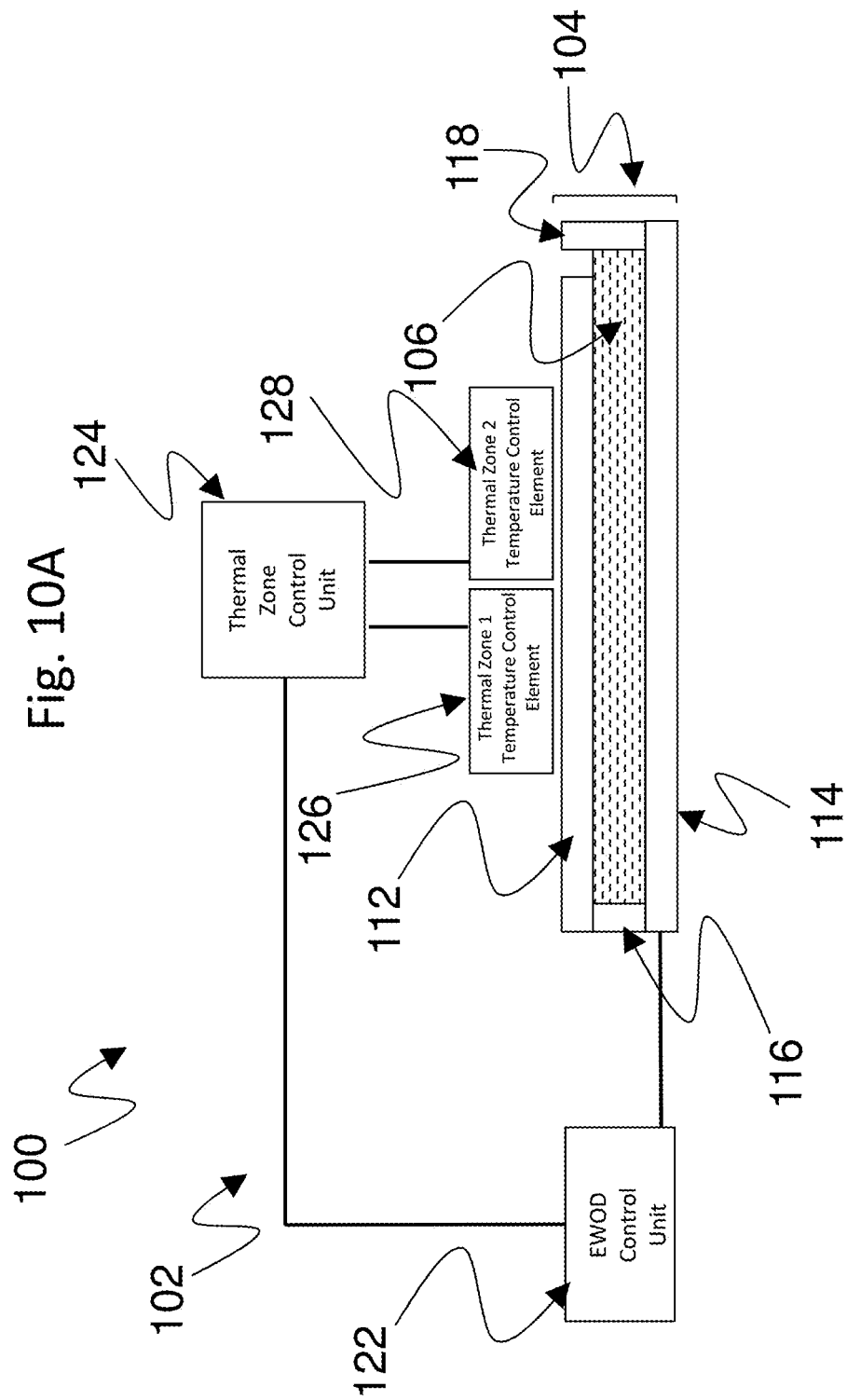
Figure 10C:
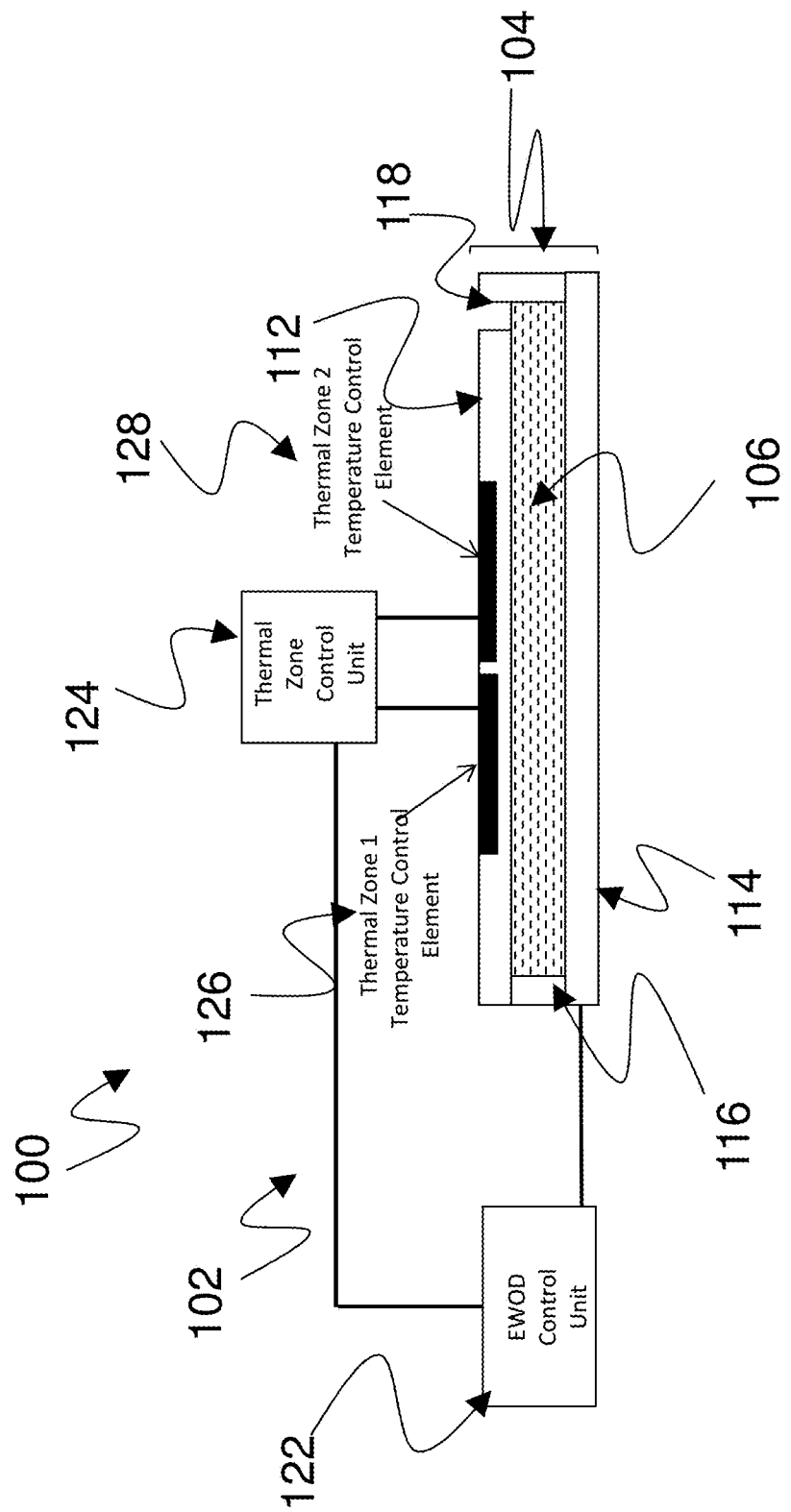
Figure 10E:
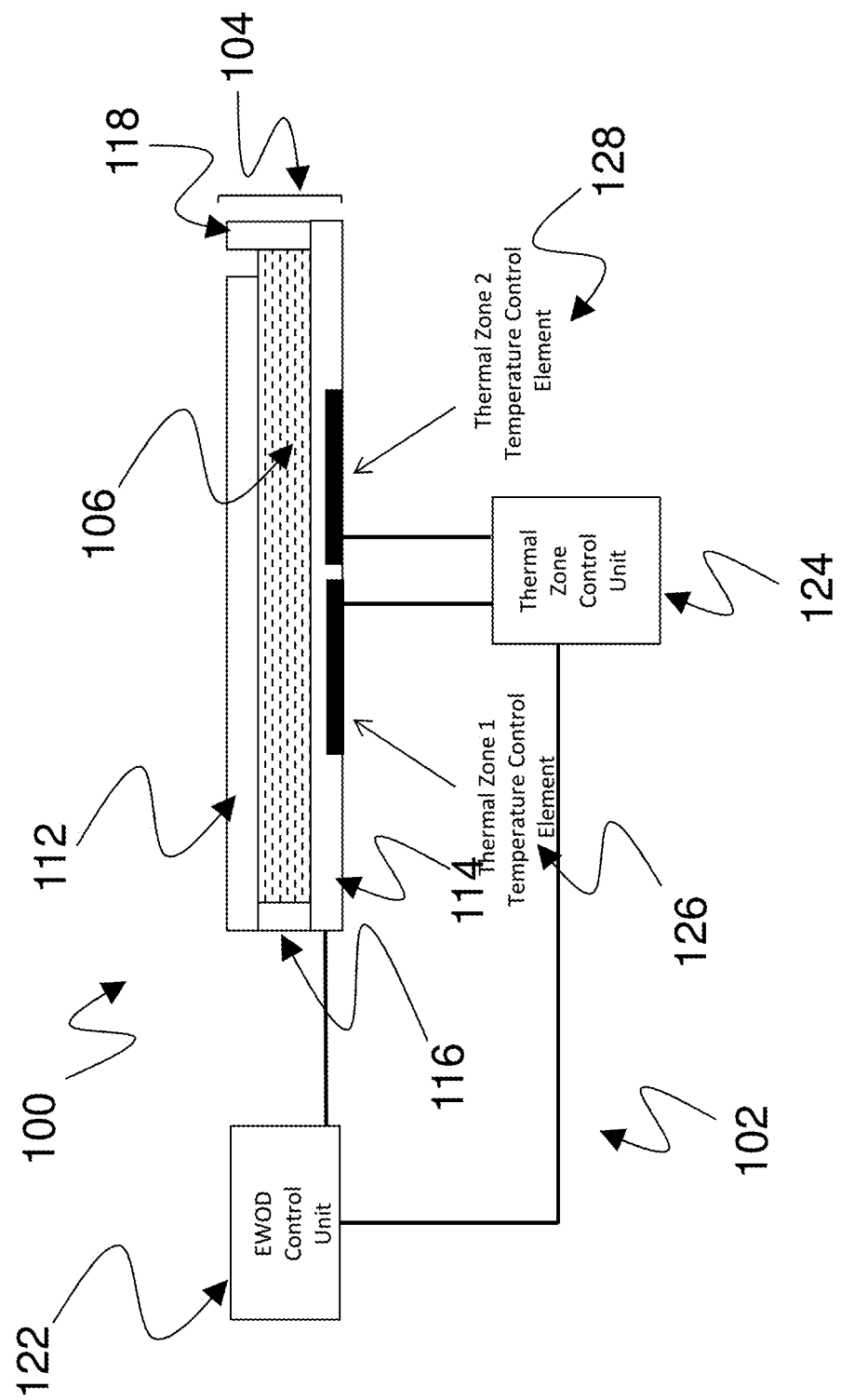

FIGS. 10A-10E demonstrate alternative arrangements of positioning of thermal control elements 126 and 128. The two or more thermal control elements may be in contact with the same surface or with opposite facing surfaces of the EWOD device, or located internally within or as part of one or both of the substrate assemblies to be closer in proximity to the EWOD channel 106. As examples of alternative positioning, in the embodiment of FIG. 10A, both thermal control elements are located on the first (top) substrate 112. In the embodiment of FIG. 10B, the first thermal control element 126 is located on the second (bottom) substrate 114, and the second thermal control element 128 is located on the first (top) substrate 112. In the embodiment of FIG. 10C, both thermal control elements are located within the first (top) substrate 112. In the embodiment of FIG. 10D, the first thermal control element 126 is located within the second (bottom) substrate 114, and the second thermal control element 128 is located within the first (top) substrate 112. In the embodiment of FIG. 10E, both thermal control elements are located within the second (bottom) substrate 114. Accordingly, any suitable configuration of positioning the thermal control elements relative to the EWOD channel may be employed.

In this manner, heating and/or cooling is applied to one or more surfaces of substrates 112 and/or 114 of the EWOD device. This in turn controls the temperature in the lateral plane between the two substrates of the EWOD device that form the EWOD channel 106 to generate the different thermal zones, such as the exemplary thermal zones 127 and 129 in FIGS. 8 and 9. The EWOD channel defines the region of the EWOD device in which the droplets are constrained and, in effect, as referenced above the temperature as controlled within the EWOD channel determines the temperature of the droplets located within said channel.

In general, in accordance with embodiments of the present invention, the thermal control unit is configured to control the thermal control elements to generate a plurality of thermal zones, i.e., at least a first thermal zone and a second thermal zone, within the channel of the EWOD device, wherein the temperature of at least one of the thermal zones is also variable with respect to time. The temperature in the channel of the EWOD device is thus varied and controlled both spatially and temporally. During the course of a chemical/biochemical reaction or sequence of reactions, droplets of a reaction mixture are moved by electrowetting between thermal zones or maintained in a given thermal zone. The temperature of a given droplet is thus a function of both its position in the channel and the time elapsed since the start of the protocol. By combining the spatial and temporal temperature control, disadvantages of conventional configurations are eliminated, and the capacity for droplet manipulations and reactions is maximized over a substantially smaller area of an EWOD device as compared to conventional configurations.

FIGS. 11-21 are graphical drawings depicting various protocols for controlling temperature within the EWOD channel of the EWOD device. Generally, in accordance with embodiments of the present invention, a microfluidic system includes a plurality of thermal control elements positioned at different spatial locations relative to the EWOD channel, with at least one of the thermal control elements being controllable to vary temperature temporally (with time). The control of the plurality of thermal control elements results in a generation of a plurality of corresponding thermal zones within the EWOD channel, with at least one thermal zone having variable temperature with time in accordance with variation of the temporally variable thermal control element. The examples of the figures are based on a microfluidic system in which the plurality of the thermal control elements includes first and second thermal control elements, with at least one of the thermal control elements being of variable temperature with time. It will be appreciated that the use of two thermal control elements is a non-limiting example, and any suitable number of thermal control elements may be employed as appropriate for any particular device or application. In addition, so long as at least one of the thermal control elements can be varied in temperature with time, the precise number of time variable thermal control elements also can be set as appropriate for any particular device or application. In other words, one or more, up to all, of the thermal control elements may be variable in temperature temporally.

Another aspect of the invention, therefore, is a control method for performing a reaction protocol using an electrowetting on dielectric (EWOD) device that combines both spatial and temperature control within the EWOD device. In exemplary embodiments, the control method includes the steps of: receiving a liquid droplet within an EWOD channel defined by the EWOD device; generating a first thermal zone at a first spatial location within the EWOD channel, the first thermal zone being controlled to have a first temperature; generating a second thermal zone at a second spatial location within the EWOD channel different from the first spatial location, the second thermal zone being controlled to have a second temperature that is variable in time; time varying the temperature of the second thermal zone; and applying actuation voltages to an element array of the EWOD device to move the liquid droplet between the first thermal zone and the second thermal zone, wherein a temperature of the liquid droplet assumes a temperature of the one of the first thermal zone or the second thermal zone in which the liquid droplet is located. The temperature of the first thermal zone may be held constant during the reaction protocol, or also may be time-varied during the reaction protocol. Temperatures of the first thermal zone and the second thermal zone may be controlled to control the temperature of the liquid droplet to vary cyclically over a plurality of thermal cycles within the reaction protocol.

The following provides an explanation as to the meanings of the various portions and line formats of the graphs in FIGS. 11-21. In all such figures, with FIG. 11 being labeled as an example, the top two graph portions depict the temperature as a function of time, i.e., a temperature profile, with respect to a first thermal zone 200 (T zone 1 or thermal zone 1) and a second thermal zone 202 (T zone 2 of thermal zone 2). The temperature profiles for the first and second thermal zones correspond to spatial thermal zones within the EWOD channel that would correspond to locations of the thermal control elements as described above (such as for example thermal zones 127 and 129). The third portion of the graphs corresponds to a resultant temperature profile of a droplet 204 (T droplet) as a function of both time and spatial location of the droplet, i.e., whether the droplet is in Thermal Zone 1 or Thermal Zone 2. T1, T2, and T3 are generalized indications of different temperatures, which may be any suitable temperatures for a given application or reaction protocol.

In the top graph portions of FIGS. 11-21 denoting the temperature profiles of the first and second thermal zones 200 and 202, a solid line portion of the graph is indicative that a droplet is located with such thermal zone, and a dashed line is indicative that a droplet is not located within such thermal zone. Similarly, in the bottom graph portion denoting the temperature profile of the droplet 204, a solid line portion of the graph is indicative that the droplet is located within a particular thermal zone, and a dashed line is indicative that the droplet is moving between thermal zones. In other words, as further explained below, the graphs show how temperature variations occur as the droplet moves spatially between the two thermal zones, and over time, with varying temperatures within the thermal zones based on control of the thermal control elements.

FIG. 11 shows exemplary temperature/time profiles for the first and second thermal zones, and the resultant temperature/time profile for a liquid droplet as it is moved by electrowetting between the two thermal zones. In this particular example, the temperature of thermal zone 1 remains constant over time at T1. The droplet is shown as initially being located within thermal zone 1, and thus the droplet begins at the temperature of T1 of thermal zone 1. During such time period, the temperature of thermal zone 2 is shifted from T3 to T2. As shown in the dashed line of the third portion of the graph, the droplet is then moved by appropriate actuation voltages from thermal zone 1 to thermal zone 2. Accordingly, the droplet cools to T2. The temperature of thermal zone 2 is then raised to T3 while the droplet remains located in thermal zone 2. The temperature of the droplet commensurately raises to T3. FIG. 11 illustrates how spatial and temporal control of temperature may be combined to access three reaction temperatures for a droplet in the EWOD channel, but using only two thermal zones. A droplet starts at temperature T1 in thermal zone 1, the droplet then moves to thermal zone 2 to experience temperature T2 (spatial temperature control), and the droplet remains in thermal zone 2 while the temperature is increased to temperature T3 (temporal temperature control). Some or all of a droplet temperature profile may be cycled through a number of times.

FIG. 11 provides a rudimentary example of the manner by which spatial temperature control is varied across the two thermal zones, and how temperature additionally is varied in time—in this example within thermal zone 2. By combining droplet temperature control via thermal zones and methods to move droplets between thermal zones by electrowetting, complex droplet temperature profiles may be achieved with minimization of the area of the device required for thermal control. The following figures are illustrative of more complex protocols that still employ only two thermal zones, as they may be tied to different portions or cycles of a biochemical/chemical reaction or sequence of reactions for any suitable reaction protocol. It will be appreciated that the various protocols of operation represent non-limiting examples.

FIGS. 12-16 are graphical drawings depicting different protocols including temperature/time profiles for first and second thermal zones, and the resultant temperature/time profile for a droplet as it is moved by electrowetting between the two thermal zones, in which the temperatures of both thermal zones are variable in time.

Figure 12:
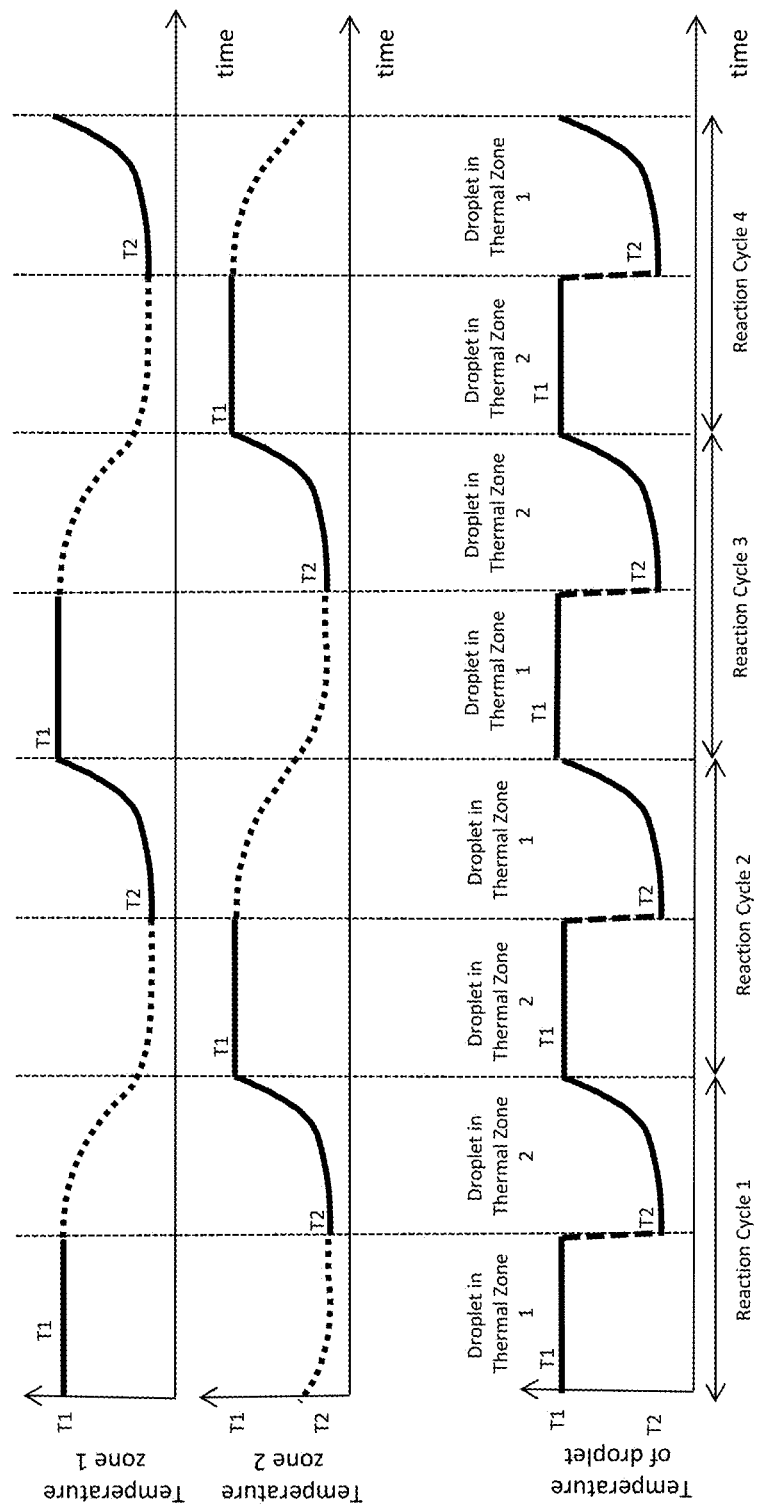
FIG. 12, FIG. 13, FIG. 14, FIG. 15, and FIG. 16 are graphical drawings depicting different protocols including temperature/time profiles for first and second thermal zones, and the resultant temperature/time profile for a droplet as it is moved by electrowetting between the two thermal zones, in which the temperatures of both thermal zones are variable in time.

Referring first to FIG. 12, a droplet starts at temperature T1 in thermal zone 1, and during such time period the temperature of thermal zone 2 is equilibrated to temperature T2. To change the droplet temperature to temperature 2, the droplet is moved rapidly by electrowetting to thermal zone 2. The rate of droplet approach to the new temperature is controlled by the speed at which the droplet can be moved between zones by the electrowetting actuation voltages. The droplet remains in thermal zone 2 while the temperature of thermal zone 2 is increased to temperature T1. The droplet temperature profile follows the temperature profile for thermal zone 2 during this period. The depicted profile is an exemplary illustration, and any temperature/time function may be imposed on the droplet. Such profile can represent a first reaction cycle (Reaction Cycle 1) that may be a portion of a complex sequence of reactions.

The droplet is then maintained at constant temperature in thermal zone 2 at temperature T1 for the start of an example second droplet reaction cycle (Reaction Cycle 2). While the droplet is in thermal zone 2, the temperature of thermal zone 1 is decreased to T2. The second reaction cycle further may include moving the droplet to thermal zone 1 by electrowetting, and the droplet then follows the temperature profile being imposed in thermal zone 1 is the last portion of the graph. This ends the second droplet temperature cycle. In this example, the droplet temperature cycles at twice the frequency of thermal zones 1 and 2. Accordingly, the droplet temperature cycles twice through thermal zones 1 and 2, and rapid droplet movement between thermal zones 1 and 2 or 2 and 1 causes a sharp temperature transition between temperatures T1 and T2. Again, any temperature/time function may be imposed on the droplet when it resides in a variable temperature zone. By moving the droplet between the two temperature zones and time varying the temperature, an efficient cycling of droplet temperature is achieved for performing a complex reaction sequence. Four full cycles are shown in this figure, but any suitable number of cycles may be employed.

Figure 13:
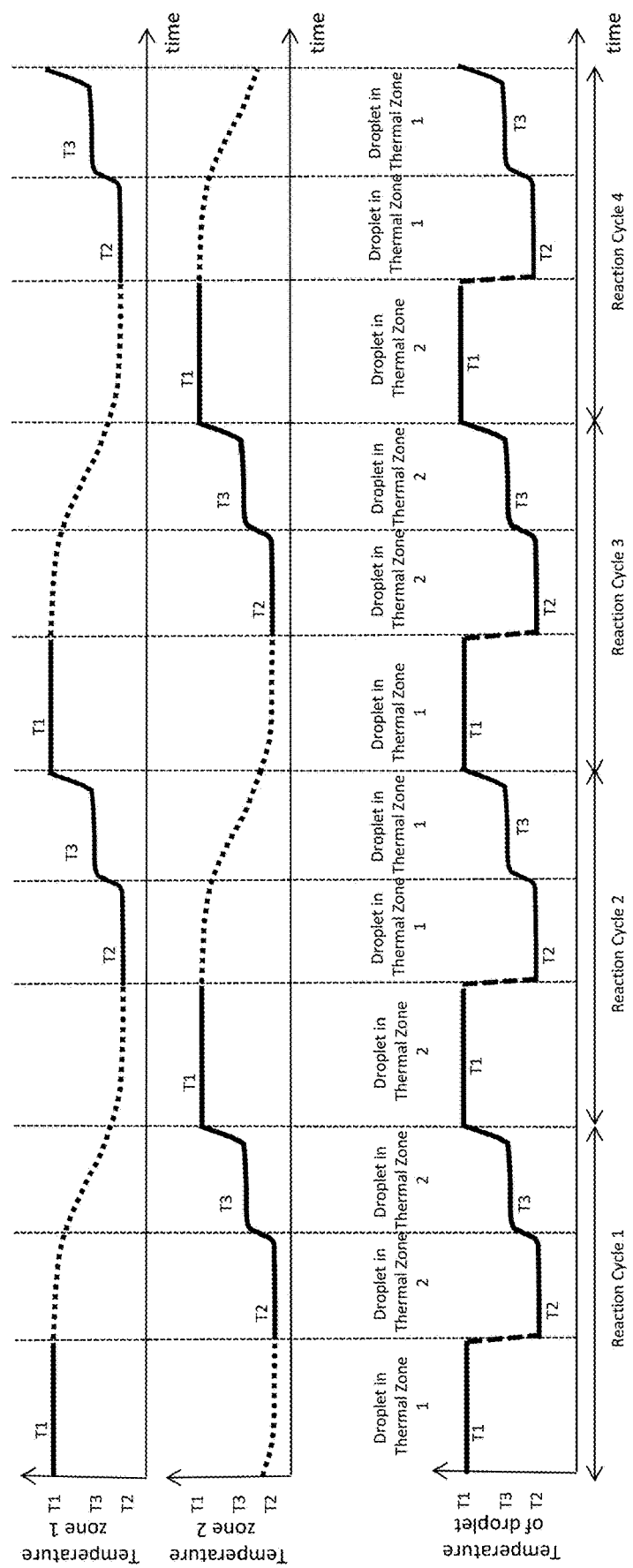

FIG. 13 shows another example of using two time-varying temperature zones to cycle the droplet temperature. Four cycles (Reaction Cycle 1, Reaction Cycle 2, Reaction Cycle 3, and Reaction Cycle 4) again are shown, but with a different temperature/time profile as compared to the previous figure. Again, any suitable number of cycles may be employed. A droplet starts at temperature T1 in thermal zone 1, and during such time period the temperature of thermal zone 2 is equilibrated to temperature T2. To change droplet temperature to temperature T2, the droplet is moved by electrowetting to thermal zone 2. In thermal zone 2 the droplet temperature is increased in a stepwise fashion based on controlled variation of the temperature in thermal zone 2, first to temperature T3, then back to temperature T1 following the required droplet temperature/time function. While the droplet is in thermal zone 2, thermal zone 1 is re-equilibrated to temperature T2. To finish the second droplet temperature cycle, the droplet is returned to thermal zone 1 which is now at temperature T2, and the droplet stays in thermal zone 2 while the temperature is increased in stepwise fashion to temperature T3 and back to temperature T1. In this example, the droplet temperature cycles at twice the frequency of the temperature of the thermal zones in repeating sequence T1 to T2 to T3. Accordingly, the droplet temperature cycles twice through thermal zones 1 and 2, and rapid droplet movement between thermal zones 1 and 2 causes a sharp temperature transition between temperatures T1 and T2.

Figure 14:
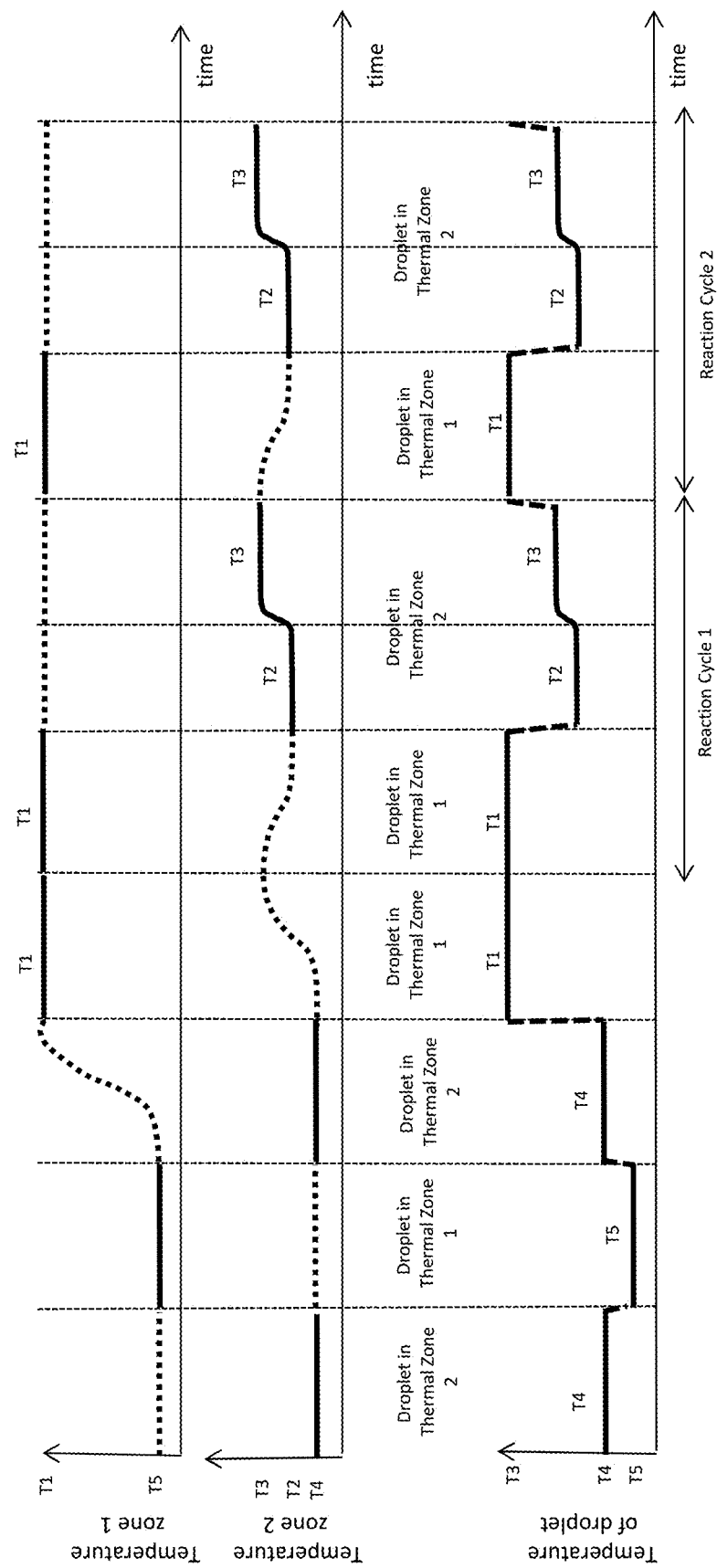

FIG. 14 shows another example of using two time-varying temperature zones to control the droplet temperature which is a variation of previous FIG. 13. In this example, a droplet undergoes a series of temperature changes before embarking on thermal cycling (the cycling begins at Reaction Cycle 1), with the thermal cycling then proceeding comparably as described for FIG. 13. This droplet temperature profile would be useful for reverse-transcription PCR as an example. Alternatively, a droplet temperature profile may include initial temperature cycling, before finishing with a number of one off temperatures.

Figure 15:
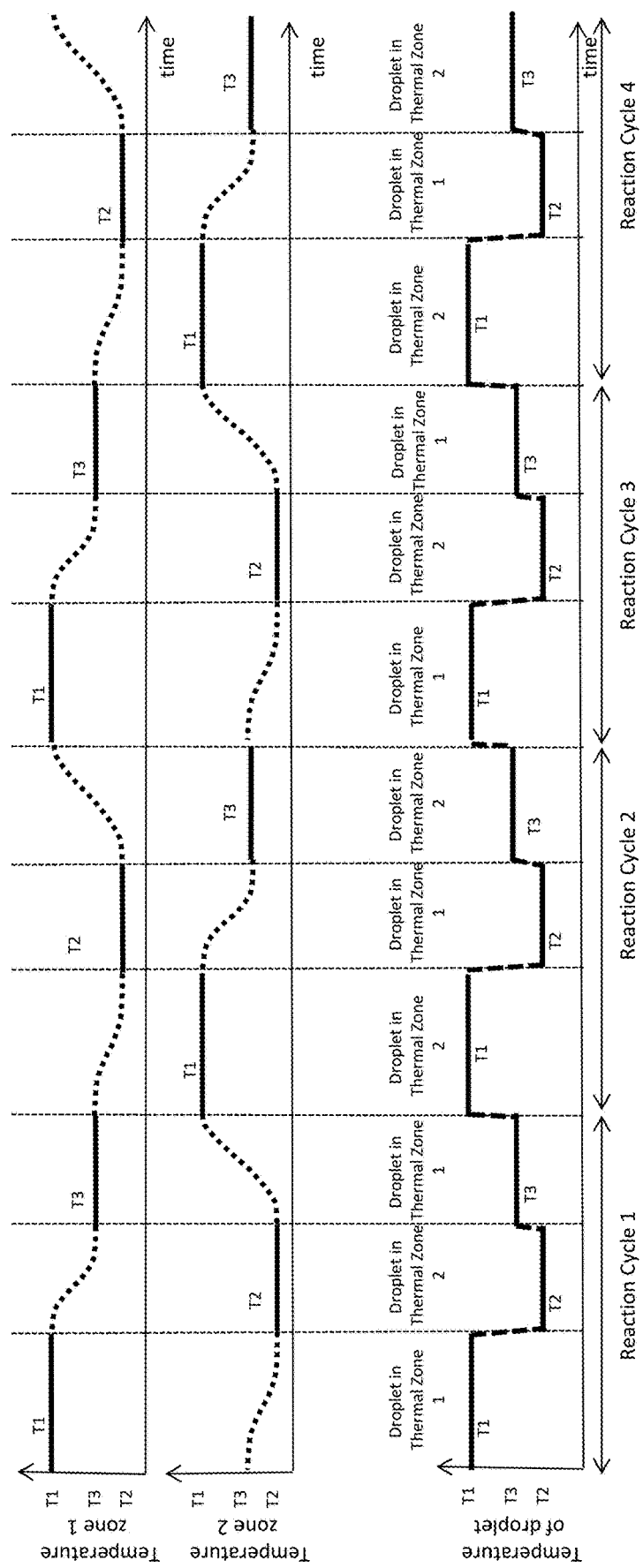

FIG. 15 shows another example of using two time-varying temperature zones to cycle the droplet temperature. Four reaction cycles (Reaction Cycle 1 Reaction Cycle 2, Reaction Cycle 3, and Reaction Cycle 4) again are shown, but with a different temperature/time profile as compared to the previous figures. Again, any suitable number of cycles may be employed. A droplet starts at temperature T1 in thermal zone 1, and during such time period the temperature of thermal zone 2 is equilibrated to temperature T2 of the reaction sequence. To change to temperature T2, the droplet is moved by electrowetting to thermal zone 2. While the droplet is in thermal zone 2 at temperature T2, thermal zone 1 is re-equilibrated to temperature T3. The droplet is then moved to thermal zone 1 at temperature T3 to end the first reaction cycle. For a second droplet temperature cycle, the droplet is returned to thermal zone 2 which is now at temperature T1 of the reaction sequence, then moved to thermal zone 1 for temperature T2 and finally thermal zone 2 for temperature T3. The droplet temperature cycles at twice the frequency of the temperature of the thermal zones in repeating sequence T1 to T2 to T3. The droplet temperature profile bears similarity to the previous figure, but the time varying of the two thermal zones and droplet location is different while achieving a comparable droplet temperature/time profile and thermal cycling.

Figure 16:
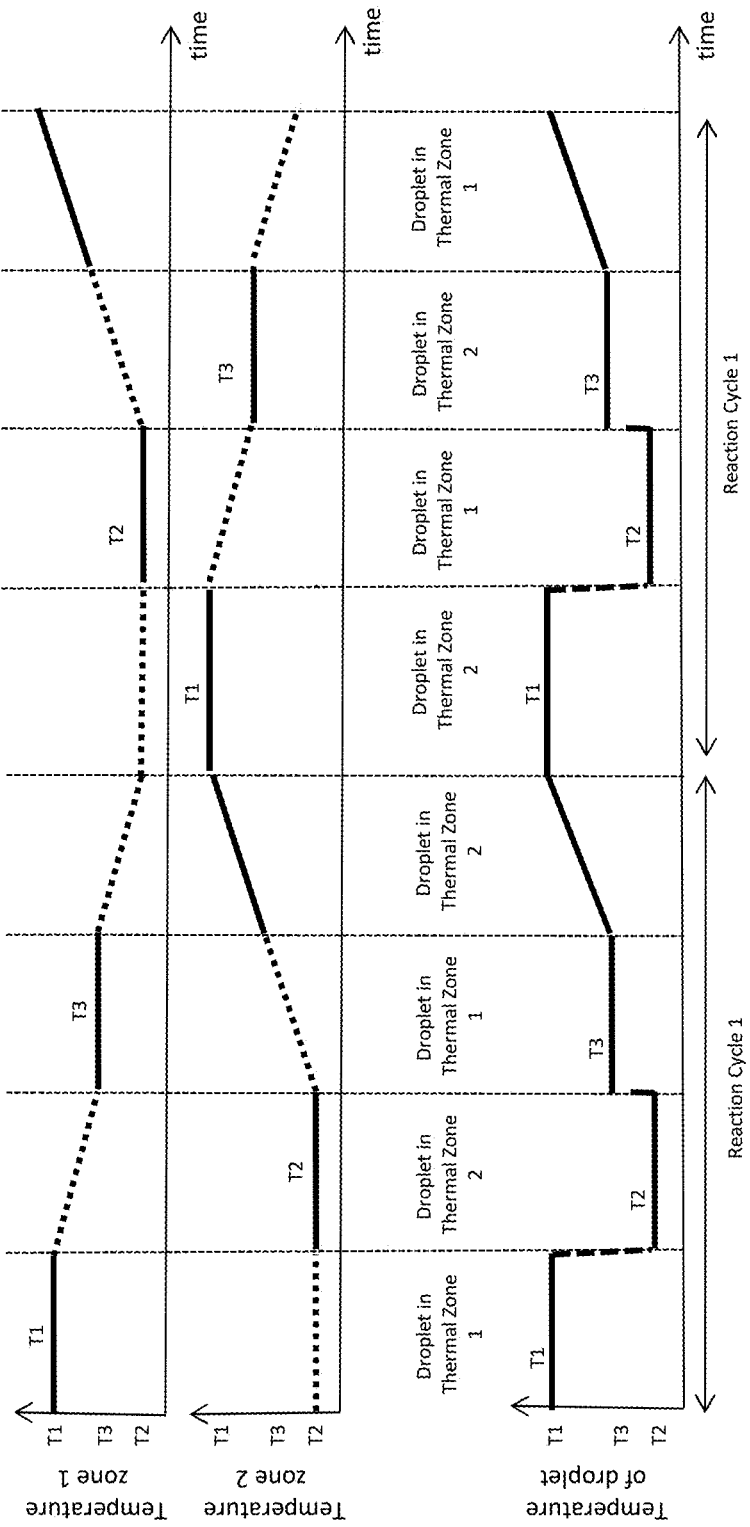

FIG. 16 shows another example of using two time-varying temperature zones to cycle the droplet temperature. A droplet starts at temperature T1 in thermal zone 1, and rapid transitions to temperature T2 and temperature T3 in sequence are then enabled via droplet movement between thermal zones 1 and 2. Finally the temperature of the droplet is modified back to temperature T1 by varying the temperature of thermal zone 2 while the droplet occupies the thermal zone. In this example, the temperature of thermal zone 2 is varied before and during the droplet occupies a given thermal zone.

FIGS. 17-20 are graphical drawings depicting different protocols including temperature/time profiles for first and second thermal zones, and the resultant temperature/time profile for a droplet as it is moved by electrowetting between the two thermal zones, in which there is one time variable temperature thermal zone and one constant temperature thermal zone.

Figure 17:
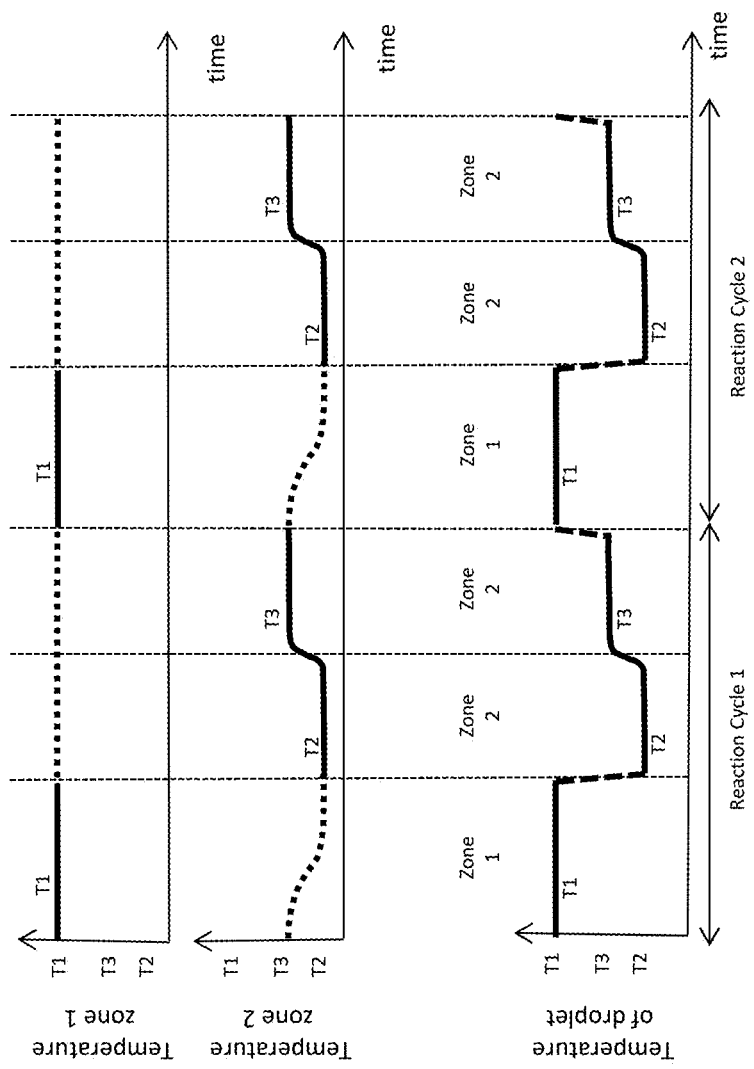
FIG. 17, FIG. 18, FIG. 19, and FIG. 20 are graphical drawings depicting different protocols including temperature/time profiles for first and second thermal zones, and the resultant temperature/time profile for a droplet as it is moved by electrowetting between the two thermal zones, in which there is one time variable temperature thermal zone and one constant temperature thermal zone.
Figure 18:
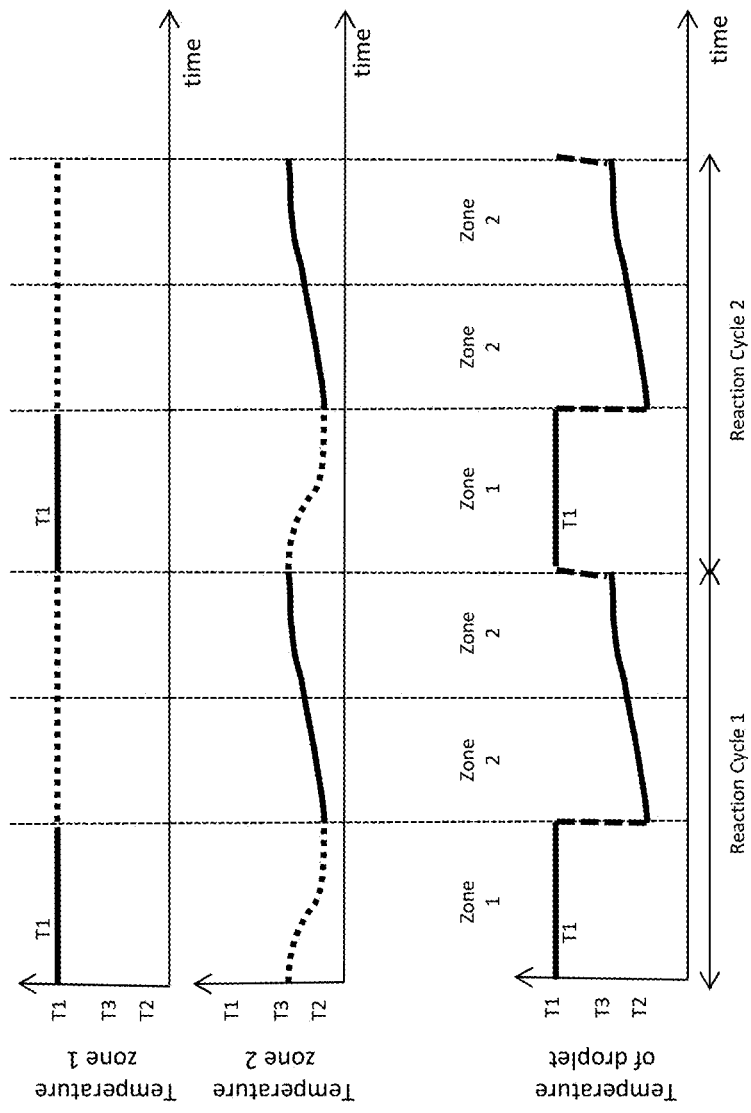

FIG. 17 essentially is comparable to FIG. 11, except to further illustrate that such a protocol can be incorporated as part of a droplet thermal cycling protocol. Two cycles are shown (Reaction Cycle 1 and Reaction Cycle 2). Again, any suitable number of cycles may be employed. The temperature of thermal zone 1 remains constant over time at T1. The droplet is shown as initially being located within thermal zone 1, and thus the droplet is at the temperature of T1 of thermal zone 1. During such time period, the temperature of thermal zone 2 is shifted from T3 to T2. The droplet is then moved from thermal zone 1 to thermal zone 2, and the droplet cools to T2. The temperature of thermal zone 2 is then raised to T3 and the temperature of the droplet commensurately raises to T3. FIG. 17 shows a stepped change between temperatures T2 and T3. In contrast, a more gradual change also can be performed from temperature T2 to T3, as illustrated in FIG. 18. Fast return to temperature T1 is then achieved by moving the droplet back to thermal zone 1. In these examples, the droplet temperature cycles at the same frequency as thermal zone 2, while the temperature in thermal zone 1 remains constant.

Figure 19:
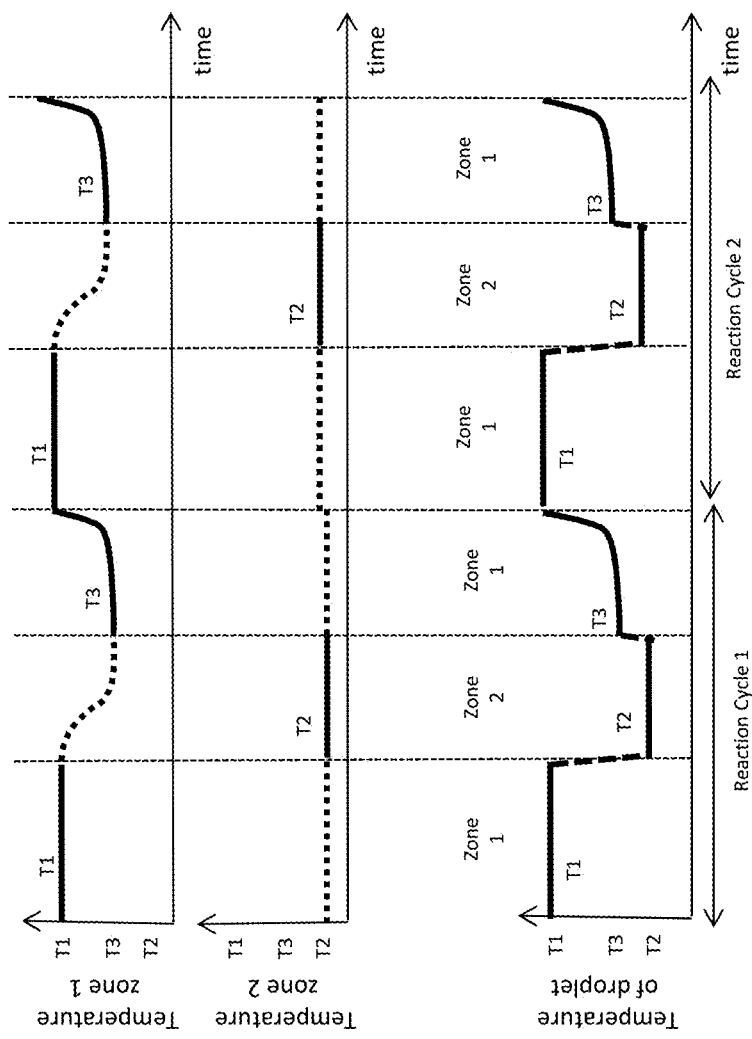

FIG. 19 shows another example of using one time-varying temperature zone and one constant temperature zone to cycle the droplet temperature. A droplet starts at temperature T1 in thermal zone 1. To change to temperature T2, the droplet is rapidly moved by electrowetting to thermal zone 2, and while the droplet is located in thermal zone 2, the temperature of thermal zone 1 is re-equilibrated to temperature T3. Rapid droplet movement to thermal zone 1 brings the droplet to temperature T3. While in thermal zone 1, the temperature of thermal zone 1, and thus the droplet, is increased from temperature T3 back to temperature T1 following the required temperature/time function for the reaction in question. The cycle may then be repeated over as many cycles as required for the reaction protocol (one additional cycle is shown in the figure for illustration). The droplet temperature cycles at the same frequency as the temperature of thermal zone 1, while the temperature in thermal zone 2 remains constant.

Figure 20:
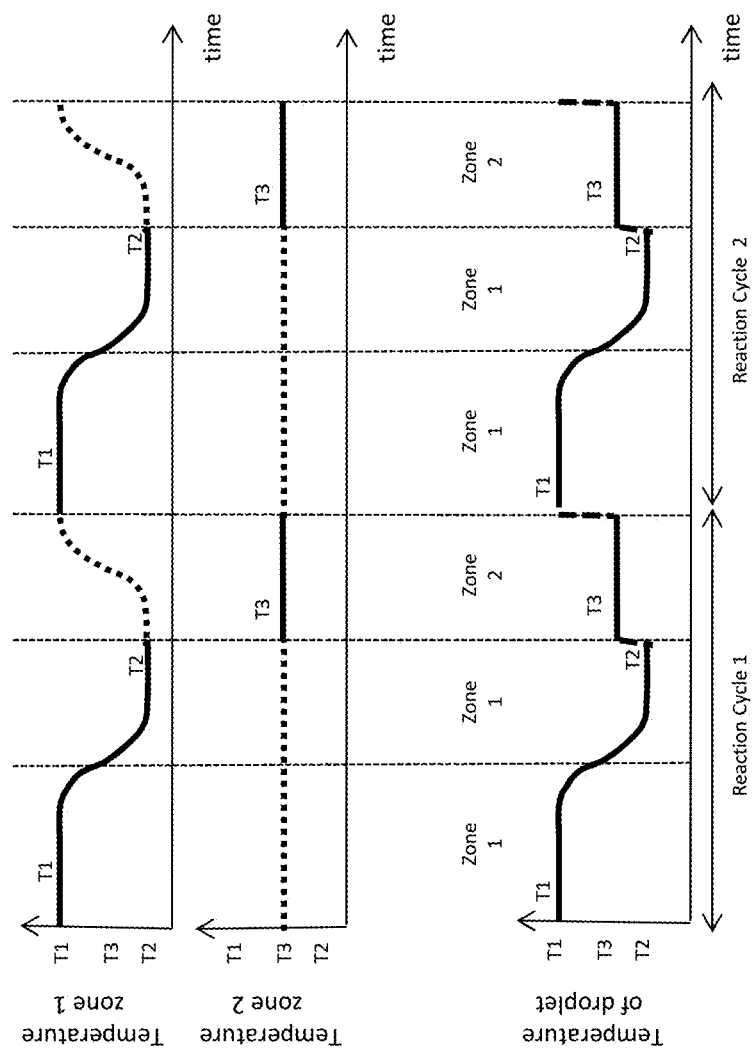

FIG. 20 shows another example of using one time-varying temperature zone and one constant temperature zone to cycle the droplet temperature. A droplet starts at temperature T1 in thermal zone 1. While the droplet is in thermal zone 1, the temperature of thermal zone 1 is decreased from temperature T1 to temperature T2 following a temperature/time profile suitable for the reaction, and the droplet temperature follows such profile. Rapid droplet movement to thermal zone 2 brings the droplet to temperature T3, insofar as the temperature of thermal zone 2 is constant at T3. While the droplet is in thermal zone 2, the temperature of thermal zone 1 re-equilibrates to temperature T1. The droplet temperature is rapidly modified to temperature T1 by moving the droplet via electrowetting to thermal zone 1. As above, the cycle may then be repeated over as many cycles as required for the reaction protocol (one additional cycle is shown in the figure for illustration). The droplet temperature cycles at the same frequency as the temperature of thermal zone 1, while temperature in thermal zone 2 remains constant.

The invention is particularly suited for temperature control in complex reaction protocols, with multiple reaction sequences that may need to be performed at different temperatures. An example of such a reaction protocol is nucleic acid amplification via PCR (polymerase chain reaction). The following describes an exemplary method for PCR thermal cycling in which a droplet is moved by electrowetting between two variable temperature thermal zones to efficiently access the three temperatures required for optimal PCR, while minimizing the area of device reserved for thermal control. FIG. 15 above in particular shows a reaction cycle utilizing three temperatures, as is suitable for PCR. A variation of such cycling applied to a PCR protocol is shown in more detail in FIG. 21.

Referring first back to FIG. 15 showing a suitable thermal cycling for PCR, as a particular example of a PCR reaction protocol, the droplet starts at temperature T1 in thermal zone 1, which for PCR can be controlled to have a first temperature corresponding to a dsDNA denaturing step at approximately 95° C. for thermal zone 1. Accordingly, the droplet is moved to thermal zone 1 and denaturing the nucleic acid is performed in thermal zone 1. While the droplet is located in thermal zone 1, the temperature of thermal zone 2 is equilibrated to temperature T2 of the reaction sequence, which for PCR can be controlled to have a second temperature corresponding to a step of annealing primers to ssDNA at approximately 60° C. To change the droplet temperature to temperature T2, the droplet is rapidly moved by electrowetting to thermal zone 2, and annealing primers to the nucleic acid is performed in thermal zone 2. While the droplet is in thermal zone 2 at temperature T2, thermal zone 1 is re-equilibrated to temperature T3, which for PCR can be controlled to a third temperature corresponding to a step of DNA elongation and polymerization at an elongation temperature of approximately 72° C. The droplet is then moved to thermal zone 1 at temperature T3, and polymerizing the nucleic acid is performed in thermal zone 1. This completes the first cycle (Reaction Cycle 1) of the PCR reaction protocol, and while the droplet is located within thermal zone 1, thermal zone 2 is re-equilibrated back to T1. For next performing a second droplet temperature cycle, the droplet is returned to thermal zone 2 which is now at temperature T1 of the reaction sequence, then moved to thermal zone 1 for temperature T2 and finally zone 2 for temperature T3, and so on. Reaction Cycles 1, 2, 3, and 4 are shown in FIG. 15 for illustration, although a typical PCR may involves approximately 40 cycles or more as may be suitable for a given PCR protocol.

Accordingly, multiple PCR cycles additionally may be performed by repeating the above PCR cycle until the nucleic acid amplification protocol is fully complete. The droplet temperature cycles at twice the frequency of the temperature of the thermal zones, and the rates of approach to each new droplet temperature are determined by the speed of droplet movement via electrowetting. The area of a device reserved for thermal management is restricted to two thermal zones, and thus the method of combining droplet movement with changing the temperatures of the thermal zones allows the three temperatures for efficient PCR to be accessed with only requiring such two spatial zones.

Figure 21:
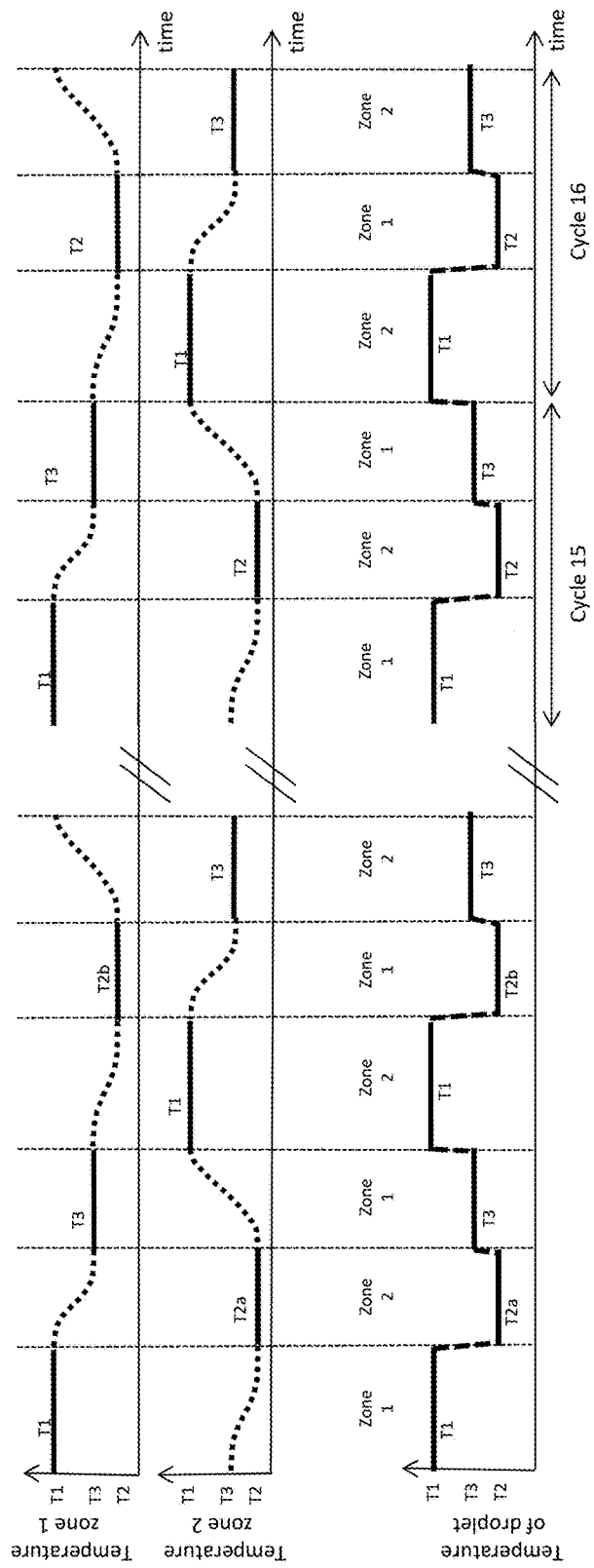
FIG. 21 is a graphical drawing depicting a touch-down PCR reaction protocol in accordance with embodiments of the present invention.
Figure 22:
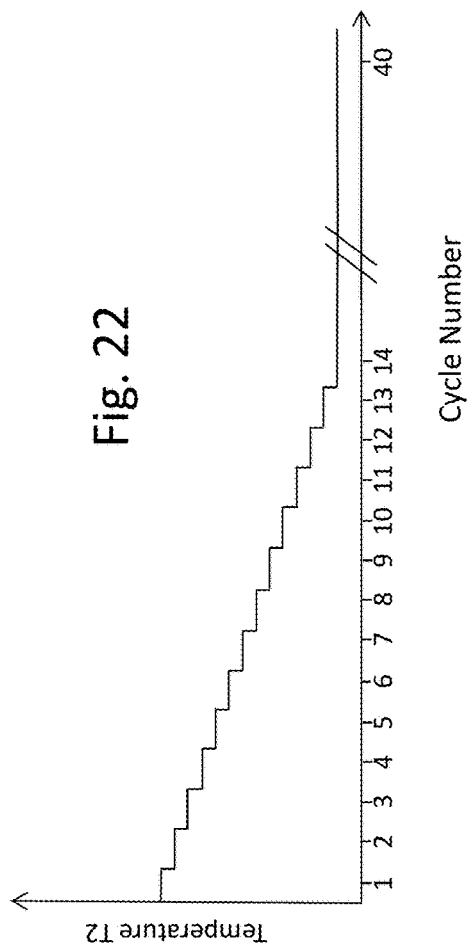
FIG. 22 is a graphical drawing depicting thermal zone temperature for a corresponding cycle number for the touch-down PCR reaction protocol of FIG. 21.

FIG. 21 more particularly is a graphical drawing depicting a variation of a PCR reaction protocol of FIG. 15 referred to in the art as touch-down PCR. In touch-down PCR, the PCR protocol described above is modified such that the primer anneal temperature, T2, is varied by 1 to 2° C. each cycle from an initial value of about 10° C. above the DNA/primer melt temperature for about the first 14 cycles of PCR. These different T2 temperatures are denoted in FIG. 21 as T2$a$, T2$b$, etc., until by cycle 15 the primer annealing temperature is T2 (e.g., about 60° C. as indicated above). The primer anneal temperature remains at T2 for subsequent cycles, e.g., Cycles 15 and 16 in FIG. 21, i.e., the anneal temperature is not further modified. This is shown in FIG. 22, which shows how the temperature T2 is varied over the first 14 cycles, and then remains at a constant temperature for the remainder of the protocol (up to for example 40 cycles or more). Accordingly, even with adjusting the primer annealing temperature over many cycles, the area of a device reserved for thermal management still is restricted to two spatial thermal zones, which permits enhanced touch-down PCR over minimal device area.

Referring back to the structural FIGS. 8-10E, any number of reaction protocols can be programmed into the control system 102. In particular, programmed reaction protocols may be provided to the EWOD control unit 122 and stored in a memory of the EWOD control unit, or transmitted as program code to the EWOD control unit 122 from some external source for execution. In accordance with such programmed reaction protocols, the EWOD control unit 122 can send control signals to the thermal zone control unit 124, which in turn generates temperature control signals for controlling the temperatures of the thermal control elements 126 and 128 to generate the thermal zones 127 and 129 within the EWOD channel 106. In addition, the EWOD control unit 122 further can generate voltage control signals to apply the actuation voltages for moving the droplets between the thermal zones in accordance with the reaction protocols, and for performing any additional associated droplet manipulation operations. In this manner, various reaction protocols can be pre-programmed into the EWOD device control system, and then executed as needed when a desired protocol is being performed, By using multiple temperature thermal zones in different spatial locations combined with temporal temperature control in one or more of such zones, numerous advantages are achieved over conventional configurations. Generally, droplets may be rapidly transitioned between different temperatures by lateral movement through the EWOD channel of the EWOD device. In addition, temporal control of one or more zones permits reassigning different spatial zones to different temperature values at different points during the protocol. This means that the same zone may be used for different reaction steps at different times in the protocol, separated by reaction steps being performed at other spatial zones while the variable zones are adjusted.

As a result, a synergistic effect of combining spatial and temporal temperature control eliminates the inefficient use of device area common in conventional configurations having only fixed temperature zones. Once droplet(s) have completed a reaction step at a given temperature within a zone and that temperature is no longer needed for subsequent steps, the temperature in this zone may be reassigned to a different value. The physical area associated with this zone may thus be re-used for an alternative droplet operation at a different temperature and at a different time. Relatedly, inefficient use of time in conventional time varying configurations is eliminated in that there is no longer a need to wait for temperature adjustments to perform subsequent reaction steps. By efficient programming of the reaction protocol into the control system, the temperature of a given zone may be varied at a time when the droplets are "busy doing something else" in a different zone, for example performing a part of the droplet manipulation protocol or an incubation step in a different location of the EWOD device.

The result is a synergistic effect by which droplet protocols of multiple sequence reactions may be performed with enhanced efficiency both in time and space, such that more droplet processing steps may be performed in a given time and in a smaller device area as compared to conventional configurations. The benefits of the present invention are particularly appreciable for devices constructed from a preferred substrate material of low thermal conductivity, such as glass or like materials. The low thermal conductivity means the thermal zones of the EWOD channel can be close together in space. Using a glass substrate, EW electrode sizes are typically smaller than when using other substrate materials (e.g. Printed Circuit Board PCB). Hence, the glass EWOD device may operate with smaller droplets and be more spatially efficient. Efficient use of the device area from a thermal point of view, and thus full realization of efficiency in an overall smaller device, is achieved.

Consequently, unexpected and enhanced results are achieved particularly in connection with EWOD devices employing glass substrates, which is preferred for a high-quality AM-EWOD device. Because of the cost associated with fabricating a TFT backplane, reducing cost by reducing chip area is a synergistic advantage achieved by the present invention. AM-EWOD devices are preferably constructed with glass substrates, since this is the standard substrate material for displays and therefore the substrate material available in AM-EWOD manufacturing factories. Furthermore, AM-EWOD devices, having a very large number of array elements and a high level of configurability, are particularly well-suited to performing complex droplet manipulation protocols such as for example PCR, including touch-down PCR. It is such high complexity droplet manipulation protocols that often require steps at a range of different temperatures, and thus particularly leverage the advantages of the present invention.

Additional advantages of the various protocols of the present invention may include one or more of the following. Three or more temperature zones may be realized with the footprint of two physical thermal zones in a system, where space needs to be conserved for increased throughput or large numbers of parallel operations. An optimum temperature profile for a droplet undergoing a biochemical/chemical reaction of a reaction sequence may be achieved by combining droplet movement between thermal zones (at different temperatures) with temperature variation of a thermal zone when occupied by a droplet. This enables the required droplet temperature profile to be optimized in the minimum space with the most favorable temperature approach rates (° C./s).

The temperature of a given thermal zone can be re-equilibrated during the time that the droplet/s is/are in another thermal zone. This given thermal zone would then be at the optimum temperature for the next step of the chemical/biochemical reaction or sequence of reactions when the droplet arrives from the other temperature zone via EWOD actuation, which saves time and therefore increases throughput.

The droplet temperature profile may be cycled by repeating the thermal zone temperature cycling. The frequency of thermal zone cycles may be the same or different from droplet temperature cycles. In addition, device area usage may be optimized for repeated reaction temperature cycles. EWOD droplet manipulation along a "there and back" one-dimensional linear path may access three or more different reaction temperatures without looped droplet movement, i.e., no two-dimensional droplets paths are required which provides for simplified operation and space savings.

The temperature of a thermal zone may be varied before, after, or during a droplet's journey through a given thermal zone. Rapid droplet temperature changes are enabled by fast movement by electrowetting between thermal zones. Droplets are small and therefore rapidly reach thermal equilibrium with their surroundings.

Considering PCR in particular, for optimum PCR the reaction mixture must cycle through three discrete temperatures typically 35 to 45 times, e.g., 95° C. to denature the double stranded DNA, 55-60° C. to anneal the primers to ssDNA, and 70-75° C. for optimum extension of the new DNA strand. The devices and methods for PCR on EWOD of the present invention provide an optimized reaction temperature profile and minimized thermal control space requirements. Further for touch-down PCR, defining a droplet temperature profile for this procedure is greatly facilitated by combining droplet temperature control via variable temperature thermal zones and methods to move droplets between the thermal zones by electrowetting. This process favors amplicon formation from primer/DNA template pairs that have the highest complementarity, reducing formation of non-specific products.

An aspect of the invention, therefore, is a microfluidic system configured for enhanced temperature control by combining spatial and temporal temperature control. In exemplary embodiments, the microfluidic system includes an electro-wetting on dielectric (EWOD) device comprising an element array configured to receive one or more liquid droplets, the element array comprising a plurality of individual array elements; a control system configured to control actuation voltages applied to the element array to perform manipulation operations as to the liquid droplets; and a plurality of thermal control elements located at different spatial locations along the EWOD device, at least one of the thermal control elements being variable in temperature with respect to time. The control system includes a thermal control unit configured to control temperatures of the plurality of thermal control elements to generate a plurality of thermal zones located at different spatial locations along the EWOD device, at least one of the thermal zones being variable in temperature with respect to time by time varying the temperature of the at least one of the thermal control elements that is variable in temperature with respect to time.

The microfluidic system may include one or more of the following features, either individually or in combination.

In an exemplary embodiment of the microfluidic system, the thermal control unit is configured to control the temperature in the at least one thermal zone variable in temperature with respect to time in accordance with a location of a liquid droplet within an EWOD channel of the EWOD device.

In an exemplary embodiment of the microfluidic system, a plurality of thermal control elements are variable in temperature with respect to time, and the thermal control unit is configured to control the plurality of variable thermal control elements to vary temperatures of a plurality of thermal zones with respect to time.

In an exemplary embodiment of the microfluidic system, the thermal control unit is configured to control at least one thermal control element to maintain at least one thermal zone at a constant temperature.

In an exemplary embodiment of the microfluidic system, the EWOD device comprises a first substrate assembly and a second substrate assembly that define an EWOD channel that receives the one or more liquid droplets, and the plurality of thermal control elements are located on an outer surface of one or both of the substrate assemblies.

In an exemplary embodiment of the microfluidic system, the EWOD device comprises a first substrate assembly and a second substrate assembly that define an EWOD channel that receives the one or more liquid droplets, and the plurality of thermal control elements are located within one or both of the substrate assemblies.

In an exemplary embodiment of the microfluidic system, the plurality of thermal control elements comprises thermal control elements that are controllable by the thermal control unit to perform one of heating or cooling.

In an exemplary embodiment of the microfluidic system, the plurality of thermal control elements comprises thermal control elements that are controllable by the thermal control unit to perform both heating and cooling.

In an exemplary embodiment of the microfluidic system, the thermal control elements comprise Joule heating elements, resistance heating elements, and/or Peltier effect elements.

In an exemplary embodiment of the microfluidic system, the microfluid system further includes comprising a droplet sensor for sensing a position of the liquid droplet within an EWOD channel of the EWOD device.

Another aspect of the invention is a control method for performing a reaction protocol using an electro-wetting on dielectric (EWOD) device having enhanced temperature control by combining spatial and temporal temperature control. In exemplary embodiments, the control method includes the steps of: receiving a liquid droplet within an EWOD channel defined by the EWOD device; generating a first thermal zone at a first spatial location within the EWOD channel, the first thermal zone being controlled to have a first temperature; generating a second thermal zone at a second spatial location within the EWOD channel different from the first spatial location, the second thermal zone being controlled to have a second temperature that is variable in time; time varying the temperature of the second thermal zone; and applying actuation voltages to an element array of the EWOD device to move the liquid droplet between the first thermal zone and the second thermal zone, wherein a temperature of the liquid droplet assumes a temperature of the one of the first thermal zone or the second thermal zone in which the liquid droplet is located. The control method may include one or more of the following features, either individually or in combination.

In an exemplary embodiment of the control method, the temperature of the second thermal zone is time varied in accordance with a location of the liquid droplet within the EWOD channel.

In an exemplary embodiment of the control method, the temperature of the second thermal zone is varied when the liquid droplet is located in the first thermal zone.

In an exemplary embodiment of the control method, the temperature of the second thermal zone is varied when the liquid droplet is located in the second thermal zone.

In an exemplary embodiment of the control method, the temperature of the first thermal zone is held constant during the reaction protocol.

In an exemplary embodiment of the control method, the control method further includes time varying the temperature in the first thermal zone during the reaction protocol.

In an exemplary embodiment of the control method, temperatures of the first thermal zone and the second thermal zone are controlled to control the temperature of the liquid droplet to vary cyclically over a plurality of droplet thermal cycles within the reaction protocol.

In an exemplary embodiment of the control method, temperatures of the first thermal zone and the second thermal zone are controlled to control the temperature of the liquid droplet to undergo a series of temperature changes prior to performing the thermal cycles.

Another aspect of the invention is a method of performing nucleic acid amplification via polymerase chain reaction (PCR) using an electro-wetting on dielectric (EWOD) device having enhanced temperature control by combining spatial and temporal temperature control. In exemplary embodiments, the PCR method includes the steps of: receiving a liquid droplet within an EWOD channel defined by the EWOD device, the liquid droplet containing a nucleic acid and performing a PCR cycle. The PCR cycle includes: generating a first thermal zone at a first spatial location within the EWOD channel, the first thermal zone being controlled to have a first temperature for performing a denaturing step, and moving the liquid droplet to the first thermal zone; denaturing the nucleic acid in the first thermal zone; generating a second thermal zone at a second spatial location within the EWOD channel different from the first spatial location, the second thermal zone being controlled to have a second temperature for performing a step of annealing primers, and moving the droplet to the second thermal zone; annealing primers of the nucleic acid in the second thermal zone; while the liquid droplet is in the second thermal zone, re-equilibrating the temperature of the first thermal zone to a third temperature for performing nucleic acid polymerization, and moving the droplet to the first thermal zone; and polymerizing the nucleic acid in the first thermal zone. The PCT method further includes performing multiple PCR cycles by repeating the PCR cycle until the nucleic acid amplification is complete.

In an exemplary embodiment, the PCR method may be a touch-down PCR method that further includes: adjusting the temperature of primer annealing in the second thermal zone between 1-2° C. starting from a temperature of 10° C. above a primer melt temperature in each PCR cycle for a first portion of multiple PCR cycles; and maintaining the temperature of primer annealing in the second thermal zone constant in each PCR cycle for a second portion of the multiple PCR cycles subsequent to the first portion of the PCR cycles.

Although the invention has been shown and described with respect to a certain embodiment or embodiments, equivalent alterations and modifications may occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein exemplary embodiment or embodiments of the invention. In addition, while a particular feature of the invention may have been described above with respect to only one or more of several embodiments, such feature may be combined with one or more other features of the other embodiments, as may be desired and advantageous for any given or particular application.

INDUSTRIAL APPLICABILITY

The described embodiments could be used to provide an enhanced AM-EWOD device. The AM-EWOD device could form a part of a lab-on-a-chip system. Such devices could be used in manipulating, reacting and sensing chemical, biochemical or physiological materials. Applications include healthcare diagnostic testing, material testing, chemical or biochemical material synthesis, proteomics, tools for research in life sciences and forensic science.

REFERENCE SIGNS LIST

10—lower substrate
12—element electrodes
12A—element electrode
12B—element electrode
14—liquid droplet
16—top substrate
18—spacer
20—non-polar surround fluid
22—insulator layer
24—first hydrophobic coating
26—contact angle
28—second hydrophobic coating
30—reference electrode
32—reader
34—cartridge
35—external sensor module
36—EWOD or AM-EWOD device
38—control electronics
40—storage device
42—cable of connecting wires
44—lower substrate
46—thin film electronics
48—element electrodes
48A—element electrode
48B—element electrode
50—electrode or element array
52—liquid droplet
54—top substrate
56—spacer
58—reference electrode
60—non-polar fluid
62—insulator layer
64—first hydrophobic coating 66—contact angle
68—second hydrophobic coating
70A—electrical load with droplet present
70B—electrical load without droplet present
72—array element circuit
74—integrated row driver
76—column driver
78—integrated sensor row addressing
80—column detection circuits
82—serial interface
84—voltage supply interface
86—number of connecting wires
88—actuation circuit
90—droplet or impedance sensing circuit
100—exemplary microfluidic system
102—control system
104—EWOD device
106—EWOD channel
108—liquid droplet
110—non-polar fluid
112—first (top) substrate assembly
114—second (bottom) substrate assembly
116—spacer
118—fluid input structure
122—EWOD control unit
124—thermal zone control unit
126—first thermal control element
127—first thermal zone
128—second thermal control element
129—second thermal zone
200—temperature profile for first thermal zone
202—temperature profile for second thermal zone
204—droplet temperature profile

What is claimed is:

1. A microfluidic system comprising:
an electro-wetting on dielectric (EWOD) device comprising an element array configured to receive one or more liquid droplets within an EWOD channel of the EWOD device, the element array comprising a plurality of individual array elements;
a control system configured to control actuation voltages applied to the element array to perform manipulation operations as to the liquid droplets; and
a plurality of thermal control elements located at different spatial locations along the EWOD device, at least one of the thermal control elements being a time variable thermal control element that is variable in temperature with respect to time;
wherein the control system includes a thermal control unit configured as an electronic processor that executes program code stored on a non-transitory computer readable medium to control temperature within the EWOD channel by controlling temperatures of the plurality of thermal control elements to perform steps of:
generating a first thermal zone at a first spatial location within the EWOD channel, the first thermal zone being controlled to have a first temperature at a first time;
generating a second thermal zone located at a second spatial location within the EWOD channel different from the first spatial location, the second thermal zone being controlled to have a second temperature at the first time, wherein the second thermal zone includes the time variable thermal control element; and
time varying the temperature of the second thermal zone to a third temperature at a second time by varying the temperature of the time variable thermal control element; and
the control system is configured to apply actuation voltages to the element array of the EWOD device to move a liquid droplet within the EWOD channel between the first thermal zone and the second thermal zone, wherein a temperature of the liquid droplet assumes a temperature of the one of the first thermal zone or the second thermal zone in which the liquid droplet is located.

2. The microfluidic system of claim 1, further comprising a droplet position sensor for sensing a position of the liquid droplet within the EWOD channel, wherein the thermal control unit is configured to control the temperature in the second thermal zone with respect to time in accordance with a location of a liquid droplet within the EWOD channel as sensed by the droplet position sensor.

3. The microfluidic system of claim 1, wherein a plurality of thermal control elements are variable in temperature with respect to time, and the thermal control unit is configured to control the plurality of variable thermal control elements to vary temperatures of a plurality of thermal zones with respect to time.

4. The microfluidic system of claim 1, wherein the thermal control unit is configured to control at least one thermal control element to maintain at least one thermal zone at a constant temperature.

5. The microfluidic system of claim 1, wherein the EWOD device comprises a first substrate assembly and a second substrate assembly that define the EWOD channel that receives the one or more liquid droplets, and the plurality of thermal control elements are located on an outer surface of one or both of the substrate assemblies.

6. The microfluidic system of claim 1, wherein the EWOD device comprises a first substrate assembly and a second substrate assembly that define the EWOD channel that receives the one or more liquid droplets, and the plurality of thermal control elements are located within one or both of the substrate assemblies.

7. The microfluidic system of claim 1, wherein the plurality of thermal control elements comprises thermal control elements that are controllable by the thermal control unit to perform one of heating or cooling.

8. The microfluidic system of claim 1, wherein the plurality of thermal control elements comprises thermal control elements that are controllable by the thermal control unit to perform both heating and cooling.

9. The microfluidic system of claim 1, wherein the thermal control elements comprise Joule heating elements, resistance heating elements, and/or Peltier effect elements.

10. A control method for performing a reaction protocol using an electro-wetting on dielectric (EWOD) device, the control method comprising the steps of:
receiving a liquid droplet within an EWOD channel defined by the EWOD device;
generating a first thermal zone at a first spatial location within the EWOD channel, the first thermal zone being controlled to have a first temperature at a first time;
generating a second thermal zone at a second spatial location within the EWOD channel different from the first spatial location, the second thermal zone being controlled to have a second temperature at the first time, wherein the temperature in the second thermal zone is variable in time;
time varying the temperature of the second thermal zone to a third temperature at a second time; and applying actuation voltages to an element array of the EWOD device to move the liquid droplet between the first thermal zone and the second thermal zone, wherein a temperature of the liquid droplet assumes a temperature of the one of the first thermal zone or the second thermal zone in which the liquid droplet is located.

11. The control method of claim 10, further comprising sensing a position of the liquid droplet within the EWOD channel, wherein the temperature of the second thermal zone is time varied in accordance with a location of the liquid droplet within the EWOD channel.

12. The control method of claim 10, wherein the temperature of the second thermal zone is varied when the liquid droplet is located in the first thermal zone.

13. The control method of claim 10, wherein the temperature of the second thermal zone is varied when the liquid droplet is located in the second thermal zone.

14. The control method of claim 10, wherein the temperature of the first thermal zone is held constant during the reaction protocol.

15. The control method of claim 10, further comprising time varying the temperature in the first thermal zone during the reaction protocol.

16. The control method of claim 10, wherein temperatures of the first thermal zone and the second thermal zone are controlled to control the temperature of the liquid droplet to vary cyclically over a plurality of droplet thermal cycles within the reaction protocol.

17. The control method of claim 16, wherein temperatures of the first thermal zone and the second thermal zone are controlled to control the temperature of the liquid droplet to undergo a series of temperature changes prior to performing the thermal cycles.

18. A method of performing nucleic acid amplification via polymerase chain reaction (PCR) using an electro-wetting on dielectric (EWOD) device, the PCR method comprising the steps of:

receiving a liquid droplet within an EWOD channel defined by the EWOD device, the liquid droplet containing a nucleic acid;

performing a PCR cycle comprising:
generating a first thermal zone at a first spatial location within the EWOD channel, the first thermal zone being controlled to have a first temperature at a first time for performing a denaturing step, and moving the liquid droplet to the first thermal zone;

denaturing the nucleic acid in the first thermal zone;

generating a second thermal zone at a second spatial location within the EWOD channel different from the first spatial location, the second thermal zone being controlled to have a second temperature at a second time for performing a step of annealing primers, and moving the droplet to the second thermal zone;

annealing primers of the nucleic acid in the second thermal zone;

while the liquid droplet is in the second thermal zone, re-equilibrating the temperature of the first thermal zone to a third temperature at a second time for performing nucleic acid polymerization, and moving the droplet to the first thermal zone; and polymerizing the nucleic acid in the first thermal zone; and performing multiple PCR cycles by repeating the PCR cycle until the nucleic acid amplification is complete.

19. The PCR method of claim 18, further comprising:
adjusting the temperature of primer annealing in the second thermal zone between 1-2° C. starting from a temperature of 10° C. above a primer melt temperature in each PCR cycle for a first portion of multiple PCR cycles; and maintaining the temperature of primer annealing in the second thermal zone constant in each PCR cycle for a second portion of the multiple PCR cycles subsequent to the first portion of the PCR cycles.

* * * * *